US012580059B2

(12) United States Patent     (10) Patent No.:   US 12,580,059 B2

McCutchan et al.     (45) Date of Patent:    Mar. 17, 2026

(54) IV COMPOUNDING SYSTEMS AND METHODS

(71) Applicant: Omnicell, Inc., Mountain View, CA (US)

(72) Inventors: Larry McCutchan, Allison Park, PA (US); Stanley Mamula, Oakmont, PA (US); Charles Marsh, Cranberry Township, PA (US)

(73) Assignee: Omnicell, Inc., Cranberry Township, PA (US)

( * ) Notice: Subject to any disclaimer, the term of this patent is extended or adjusted under 35 U.S.C. 154(b) by 37 days.

(21) Appl. No.: 17/738,869

(22) Filed: May 6, 2022

(65) Prior Publication Data

US 2022/0262473 A1     Aug. 18, 2022

Related U.S. Application Data

(62) Division of application No. 15/827,336, filed on Nov. 30, 2017, now Pat. No. 11,335,444.

(51) Int. Cl.
    *G16H 20/10*       (2018.01)
    *A61J 3/00*        (2006.01)
              (Continued)

(52) U.S. Cl.
    CPC ............. *G16H 20/10* (2018.01); *A61J 3/002* (2013.01); *A61M 5/00* (2013.01); *G16H 40/20* (2018.01); *G06F 3/0482* (2013.01)

(58) Field of Classification Search
    CPC ......... G16H 20/10; G16H 40/20; A61J 3/002; A61M 5/00; A61M 2205/3393; G06F 3/0482
              (Continued)

(56) References Cited

U.S. PATENT DOCUMENTS

| | | |
|---|---|---|
| 6,711,460 B1 | 3/2004 | Reese |
| 6,975,924 B2 | 12/2005 | Kircher et al. |

(Continued)

FOREIGN PATENT DOCUMENTS

| | | |
|---|---|---|
| AU | 2018370976 | 5/2019 |
| AU | 2018374994 | 6/2019 |

(Continued)

OTHER PUBLICATIONS

Application No CN201880077558.6, Office Action, Mailed on Feb. 20, 2023, 6 pages (no English translation available).

(Continued)

*Primary Examiner* — Jason B Dunham
*Assistant Examiner* — Kimberly A. Sass
(74) *Attorney, Agent, or Firm* — Lee & Hayes, P.C.

(57) ABSTRACT

Systems and methods of compounding of medication include a user interface that enables efficient design of compounding workflows and protocols. A user can select a workflow type from a number of workflow types differentiated at least in part by the vehicle in which a compounded pharmaceutical is to be delivered, and the user may also specify a compounding device. Options are presented and the steps of a workflow in accordance with the workflow type and options is displayed and updated in real time as options are selected. A protocol can be constructed by inserting information into the workflow based on a specification of a particular pharmaceutical to be compounded.

20 Claims, 26 Drawing Sheets

(51) Int. Cl.
    *A61M 5/00*         (2006.01)
    *G16H 40/20*      (2018.01)
    *G06F 3/0482*      (2013.01)

(58) Field of Classification Search
    USPC .......................................................... 705/2
    See application file for complete search history.

(56)              References Cited

U.S. PATENT DOCUMENTS

| | | |
|---|---|---|
| 7,579,592 B2 | 8/2009 | Kaushal |
| 7,706,915 B2 | 4/2010 | Mohapatra et al. |
| 8,215,557 B1 | 7/2012 | Reno et al. |
| 8,315,887 B2 | 11/2012 | Berkelhamer et al. |
| 8,431,404 B2 | 4/2013 | Spence et al. |
| 8,554,579 B2 | 10/2013 | Tribble et al. |
| 8,639,525 B2 | 1/2014 | Levine et al. |
| 8,666,780 B2 | 3/2014 | Berkelhamer et al. |
| 9,069,887 B2 | 6/2015 | Gupta et al. |
| 9,311,807 B2 | 4/2016 | Schultz et al. |
| 9,375,079 B2 | 6/2016 | Ranalletta et al. |
| 9,959,628 B2 | 5/2018 | Mutti et al. |
| 9,978,139 B2 | 5/2018 | Kriheli et al. |
| 10,181,186 B2* | 1/2019 | Kriheli ................. G06V 30/224 |
| 10,336,477 B2 | 7/2019 | Perazzo et al. |
| 10,596,319 B2 | 3/2020 | Trovato et al. |
| 10,853,938 B2 | 12/2020 | Sandmann et al. |
| 10,967,125 B2 | 4/2021 | Trovato et al. |
| 10,991,264 B2 | 4/2021 | Trovato et al. |
| 11,335,444 B2 | 5/2022 | McCutchan et al. |
| 12,017,046 B2 | 6/2024 | Trovato et al. |
| 12,042,632 B2 | 7/2024 | Trovato et al. |
| 12,343,503 B2 | 7/2025 | Trovato et al. |
| 12,397,114 B2 | 8/2025 | Trovato et al. |
| 2001/0041968 A1 | 11/2001 | Hamilton |
| 2002/0035412 A1 | 3/2002 | Kircher |
| 2004/0078231 A1 | 4/2004 | Wilkes |
| 2006/0000470 A1 | 1/2006 | Clarke et al. |
| 2006/0149416 A1 | 7/2006 | Mohapatra et al. |
| 2006/0259195 A1 | 11/2006 | Eliuk et al. |
| 2007/0047980 A1 | 3/2007 | Limer et al. |
| 2007/0088590 A1 | 4/2007 | Berkelhamer et al. |
| 2007/0093935 A1 | 4/2007 | Fu |
| 2007/0177778 A1 | 8/2007 | Massaro |
| 2007/0257192 A1 | 11/2007 | Nishino et al. |
| 2008/0125897 A1 | 5/2008 | DiGianfilippo |
| 2008/0140444 A1 | 6/2008 | Karkanias et al. |
| 2008/0195246 A1 | 8/2008 | Tribble et al. |
| 2009/0154764 A1 | 6/2009 | Khan et al. |
| 2009/0188311 A1 | 7/2009 | Cadieux et al. |
| 2009/0198208 A1 | 8/2009 | Stavsky et al. |
| 2009/0222817 A1 | 9/2009 | Faatz et al. |
| 2010/0094653 A1 | 4/2010 | Tribble et al. |
| 2010/0097451 A1 | 4/2010 | Bruce et al. |
| 2010/0118130 A1 | 5/2010 | Harris et al. |
| 2010/0131097 A1 | 5/2010 | Young et al. |
| 2011/0056290 A1 | 3/2011 | Bryant et al. |
| 2011/0211067 A1 | 9/2011 | McKay et al. |
| 2012/0002042 A1 | 1/2012 | Okuma |
| 2012/0173254 A1 | 7/2012 | Korhnak et al. |
| 2012/0173255 A1 | 7/2012 | Korhnak et al. |
| 2012/0199239 A1 | 8/2012 | Okuda et al. |
| 2012/0241043 A1 | 9/2012 | Perazzo et al. |
| 2013/0058550 A1 | 3/2013 | Tanimoto et al. |
| 2013/0142406 A1 | 6/2013 | Lang et al. |
| 2013/0188038 A1 | 7/2013 | Tanimoto et al. |
| 2013/0204637 A1* | 8/2013 | Vanderveen ........... G16H 20/13 |
| | | 705/2 |
| 2014/0062882 A1 | 3/2014 | Ozawa et al. |
| 2014/0156294 A1 | 6/2014 | Tribble et al. |
| 2014/0157731 A1 | 6/2014 | Perazzo et al. |
| 2014/0177932 A1 | 6/2014 | Milne et al. |
| 2014/0214199 A1 | 7/2014 | Utech et al. |
| 2014/0233797 A1 | 8/2014 | Hodder et al. |
| 2014/0350946 A1 | 11/2014 | Klomp |
| 2015/0125945 A1 | 5/2015 | Holmes et al. |

| | | |
|---|---|---|
| 2015/0250678 A1 | 9/2015 | Eliuk et al. |
| 2015/0251779 A1 | 9/2015 | Tachibana et al. |
| 2015/0309505 A1 | 10/2015 | Popp |
| 2016/0001003 A1 | 1/2016 | Perazzo et al. |
| 2016/0071265 A1 | 3/2016 | Sandmann et al. |
| 2016/0073019 A1 | 3/2016 | Nowicki et al. |
| 2016/0092639 A1 | 3/2016 | Padmani et al. |
| 2016/0140315 A1 | 5/2016 | Diaz et al. |
| 2016/0161402 A1 | 6/2016 | Micheels et al. |
| 2016/0200462 A1 | 7/2016 | Kriheli et al. |
| 2016/0210437 A1 | 7/2016 | Padmani et al. |
| 2016/0232325 A1 | 8/2016 | Utech et al. |
| 2016/0247277 A1 | 8/2016 | Kriheli et al. |
| 2017/0028130 A1 | 2/2017 | Perazzo et al. |
| 2017/0056603 A1 | 3/2017 | Cowan et al. |
| 2017/0056604 A1 | 3/2017 | Cowan et al. |
| 2017/0286635 A1* | 10/2017 | Harshbarger, III .... G16H 20/10 |
| 2017/0333623 A1 | 11/2017 | Kamen et al. |
| 2017/0372034 A1 | 12/2017 | Tribble et al. |
| 2018/0008787 A1 | 1/2018 | Schriver et al. |
| 2018/0091745 A1 | 3/2018 | Holmes |
| 2018/0108435 A1 | 4/2018 | Brown et al. |
| 2018/0154088 A1 | 6/2018 | Broselow |
| 2019/0041318 A1 | 2/2019 | Wissmann et al. |
| 2019/0311490 A1 | 10/2019 | Crawford et al. |
| 2019/0333618 A1* | 10/2019 | Tribble ................... G16H 20/17 |
| 2020/0261318 A1 | 8/2020 | Ranalletta et al. |
| 2021/0178071 A1 | 6/2021 | Trovato et al. |
| 2021/0205537 A1 | 7/2021 | Trovato et al. |

FOREIGN PATENT DOCUMENTS

| | | | | |
|---|---|---|---|---|
| AU | 2018374995 | 6/2019 | | |
| BR | 112020008928 | 10/2020 | | |
| BR | 112020009921 | 11/2020 | | |
| CA | 3080903 | 5/2019 | | |
| CA | 3081620 | 6/2019 | | |
| CA | 3082168 | 6/2019 | | |
| CN | 1175539 A | 3/1998 | | |
| CN | 203224706 U | 10/2013 | | |
| CN | 105593873 A | 5/2016 | | |
| CN | 102682264 B | 11/2016 | | |
| CN | 106716085 A | 5/2017 | | |
| CN | 107076606 A | 8/2017 | | |
| CN | 111433692 | 7/2020 | | |
| CN | 111492337 | 8/2020 | | |
| CN | 111448583 | 7/2021 | | |
| EP | 2816346 | 12/2014 | | |
| EP | 2983993 | 2/2016 | | |
| EP | 3714426 | 9/2020 | | |
| EP | 3717978 | 10/2020 | | |
| EP | 3718066 | 10/2020 | | |
| FR | 3007611 | 12/2014 | | |
| JP | 0979824 A | 3/1997 | | |
| JP | 2004208842 A | 7/2004 | | |
| JP | 2006502814 | 1/2006 | | |
| JP | 2006296912 A | 11/2006 | | |
| JP | 2007515213 A | 6/2007 | | |
| JP | 5710600 B2 | 3/2015 | | |
| JP | 2015-123205 | 7/2015 | | |
| JP | 2015-167646 | 9/2015 | | |
| JP | 2017527377 A | 9/2017 | | |
| JP | 2017534995 A | 11/2017 | | |
| JP | 2017-537377 | 12/2017 | | |
| JP | 2021-503976 | 2/2021 | | |
| JP | 2021-505233 | 2/2021 | | |
| JP | 2021-505234 | 2/2021 | | |
| KR | 20150052197 A | 5/2015 | | |
| KR | 20150069028 A | 6/2015 | | |
| KR | 20170129107 A | 11/2017 | | |
| KR | 20200093616 | 8/2020 | | |
| WO | 03058507 | 7/2003 | | |
| WO | 2004036481 | 4/2004 | | |
| WO | 2004053468 | 6/2004 | | |
| WO | WO-2008057854 A2 * | 5/2008 | ............. | G16H 40/20 |
| WO | WO-2011095900 A1 * | 8/2011 | ............. | G16H 40/20 |
| WO | 2011112606 A1 | 9/2011 | | |
| WO | 2012/073774 | 6/2012 | | |
| WO | 2013/180127 | 12/2013 | | |

(56) References Cited

FOREIGN PATENT DOCUMENTS

| WO | 2014065872 | A1 | 5/2014 | |
| WO | 2014/119994 | | 8/2014 | |
| WO | 2014123147 | | 8/2014 | |
| WO | 2014138607 | A1 | 9/2014 | |
| WO | WO-2014190200 | A1 * | 11/2014 | ......... G06F 19/3456 |
| WO | WO2016040334 | A1 | 3/2016 | |
| WO | 2017095702 | A1 | 6/2017 | |
| WO | 2017/116961 | | 7/2017 | |
| WO | 2019103847 | | 5/2019 | |
| WO | 2019109048 | | 6/2019 | |
| WO | 2019109052 | | 6/2019 | |

OTHER PUBLICATIONS

U.S. Appl. No. 15/827,336, Advisory Action, Mailed on Apr. 23, 2021, 5 pages.
U.S. Appl. No. 15/827,336, "Corrected Notice of Allowability", Mar. 11, 2022, 2 pages.
U.S. Appl. No. 15/865,038, Advisory Action, Mailed on Jan. 29, 2021, 3 pages.
U.S. Appl. No. 17/184,047, Final Office Action, Mailed on Dec. 8, 2022, 18 pages.
Application No. AU2018374994, "Notice of Acceptance", Jun. 11, 2021, 3 pages.
Application No CN201880076771.5 , Office Action, Mailed on Oct. 24, 2022, 10 pages (no English translation).
Application No. EP18882550.9, Office Action, Mailed on Nov. 7, 2022, 9 pages.
Application No. IT102017000134813 , Office Action, Mailed on Aug. 28, 2018, 11 pages.
Application No. JP2020-529543, Notice of Allowance, Mailed on Nov. 15, 2022, 6 pages.
Application No. KR10-2020-7018537, Notice of Decision to Grant, Mailed on Nov. 29, 2022, 4 pages.
U.S. Appl. No. 17/184,047 , Notice of Allowance, Mailed on Sep. 18, 2023, 8 pages.
AU2018370976 , "First Examination Report", May 3, 2023, 3 pages.
AU2018374995 , "First Examination Report", Sep. 25, 2023, 5 pages.
Application No. CN201880076771.5 , Office Action, Mailed on Sep. 28, 2023, 6 pages.
Application No. CN201880077558.6 , Office Action, Mailed on Aug. 4, 2023, 4 pages.
Application No. EP18884766.9 , Office Action, Mailed on Jul. 25, 2023, 10 pages.
Application No. KR10-2020-7018009 , Office Action, Mailed on Aug. 8, 2023, 12 pages.
U.S. Appl. No. 17/209,625, "Corrected Notice of Allowability", Feb. 2, 2023, 2 pages.
Application No. EP18880996.6, Office Action, Mailed on Jan. 31, 2023, 8 pages.
Application No. JP2020-524191, Notice of Allowance, Mailed on Feb. 1, 2023, 6 pages.
"IDS Imaging Development Systems GmbH", data sheet for product No. UI-5481LE-M, Feb. 20, 2017, pp. 1-3. Accessed from the internet: https://en.ids-imaging.com/store/ui-5481le.html.
"Basler dart Area Scan Cameras" brochure, Jan. 2017, pp. 1-8, No. 7. Accessed from the internet: https://www.baslerweb.com/fp-1486541807/media/downloads/documents/brochure/BAS1701_dart_Broschuere_EN_SAP5052_web.pdf.
PCT/US2018/063493 received an International Search Report and Written Opinion mailed Feb. 21, 2019, 8 pages.
PCT/US2018/063500 received an International Search Report and Written Opinion mailed Feb. 7, 2019, 14 pages.
PCT/US2018/063500 received an International Preliminary Report on Patentability mailed Jun. 11, 2020, 12 pages.
U.S. Appl. No. 15/865,038 received a Non-Final Office Action mailed Mar. 8, 2019, 17 pages.
PCT/US2018/059641 received an International Search Report and Written Opinion mailed Mar. 22, 2019, 10 pages.
IT 102017000134813 received an office action mailed Apr. 9, 2018, 11 pages.
U.S. Appl. No. 15/865,038 received a Non-Final Office Action mailed Oct. 4, 2019, 18 pages.
U.S. Appl. No. 16/207,016 received a Corrected Notice of Allowance mailed Dec. 9, 2019, 2 pages.
U.S. Appl. No. 16/207,016 received a Notice of Allowance mailed Oct. 30, 2019, 9 pages.
U.S. Appl. No. 15/865,038 received a Non-Final Office Action mailed May 13, 2020, 21 pages.
U.S. Appl. No. 16/792,519 received a Non-Final Office Action mailed Sep. 4, 2020, 8 pages.
U.S. Appl. No. 15/865,038 received a Final Office Action mailed Oct. 23, 2020, 20 pages.
U.S. Appl. No. 16/792,519 received a Notice of Allowance mailed Nov. 25, 2020, 7 pages.
European patent application 18884766.9 received an Extended European Search Report, mailed Jul. 20, 2021, 10 pages.
European Application No. 18880996.6 received an Extended European Search Report, mailed Aug. 23, 2021, 10 pages.
Japan Application No. JP2020-529548 received a Final Office Action, mailed on Jan. 18, 2022, 7 pages (pp. 1-4 English translation, pp. 5-7 original document).
Korean Application No. KR10-2020-7018537 received an Office Action, mailed on Dec. 21, 2021, 14 pages (pp. 1-7 English Translation, pp. 8-14 original document).
U.S. Appl. No. 15/827,336 received a Non-Final Office Action mailed Aug. 7, 2020, 24 pages.
U.S. Appl. No. 15/827,336 received a Final Office Action mailed Jan. 25, 2021, 26 pages.
U.S. Appl. No. 15/827,336 received a Non-Final Office Action mailed Jun. 15, 2021, 24 pages.
U.S. Appl. No. 15/827,336 received a Notice of Allowance mailed Jan. 21, 2022, 8 pages.
U.S. Appl. No. 15/865,038 received a Notice of Allowance mailed on Mar. 3, 2021, 12 pages.
U.S. Appl. No. 17/184,047 received a Non-Final Office Action mailed Oct. 28, 2021, 15 pages.
U.S. Appl. No. 17/184,047 received a Final Office Action mailed Apr. 14, 2022, 15 pages.
U.S. Appl. No. 17/209,625 received a Non-Final Office Action mailed Feb. 17, 2022, 16 pages.
PCT/US2018/059641 received an International Preliminary Report on Patentability mailed Jun. 4, 2020, 9 pages.
PCT/US2018/063493 received an International Preliminary Report on Patentability mailed Jun. 11, 2020, 8 pages.
Japan patent application 2020-524191 received an office action mailed Nov. 2, 2021, 10 pages (pp. 1-6 English translation, pp. 7-10 original document).
Japan Application No. JP2020-529548 received an office action mailed on Jun. 15, 2021, 4 pages (pp. 1-4 English translation, pp. 5-8 original document).
European Application No. 18882550.9 received an Extended European Search Report mailed Jul. 6, 2021, 10 pages.
Canada Patent Application No. 3082168 received an Office Action mailed Sep. 1, 2021, 4 pages.
Australia Patent Application No. 2018374994 received a First Examination Report mailed Dec. 16, 2020, 4 pages.
U.S. Appl. No. 17/184,047 received an Advisory Action Before the Filing of an Appeal Brief mailed Jun. 27, 2022, 5 pages.
Canada Patent Application No. 3082168 received a Notice of Allowance mailed Jul. 15, 2022, 50 pages.
Japan Patent Application No. 2020-524191 received an Office Action mailed Jul. 26, 2022, 12 pages (pp. 1-7 English translation, pp. 8-12 original document).
U.S. Appl. No. 17/209,625 received a Final Office Action mailed Aug. 4, 2022, 9 pages.
Japan Patent Application No. 2020-529543 received an Office Action mailed Aug. 2, 2022, 13 pages (pp. 1-6 English translation, pp. 7-13 original document).

(56)                    References Cited

OTHER PUBLICATIONS

Japan Patent Application No. 2020-529548 received a Notice of Allowance mailed Aug. 9, 2022, 6 pages.
Korea Patent Application 10-2020-7018537 received a Final Office Action mailed Jul. 28, 2022, 8 pages (pp. 1-4 English translation, pp. 5-8 original document).
U.S. Appl. No. 17/184,047 received a Non-Final Office Action mailed Aug. 18, 2022, 16 pages.
U.S. Appl. No. 17/184,047 , "Corrected Notice of Allowability", Mar. 7, 2024, 4 pages.
U.S. Appl. No. 17/184,047 , Notice of Allowance, Mailed on Jan. 18, 2024, 8 pages.
U.S. Appl. No. 18/168,616 , "Corrected Notice of Allowability", Apr. 17, 2024, 2 pages.
U.S. Appl. No. 18/168,616 , Notice of Allowance, Mailed on Mar. 4, 2024, 10 pages.
AU2018370976 , "Notice of Acceptance", May 3, 2024, 3 pages.
AU2018370976 , "Second Examination Report", Jan. 30, 2024, 3 pages.
Application No. CA3,080,903 , Office Action, Mailed on Nov. 1, 2023, 6 pages.
Application No. CA3081620 , Office Action, Mailed on Feb. 21, 2024, 9 pages.
Application No. CN201880077558.6 , Notice of Decision to Grant, Mailed on Nov. 16, 2023, 2 pages.
Application No. EP18880996.6 , Office Action, Mailed on Dec. 8, 2023, 6 pages.
Application No. KR10-2020-7018009 , Notice of Allowance, Mailed on Feb. 22, 2024, 8 pages.
Application No. KR10-2020-7018806 , Notice of Decision to Grant, Mailed on Mar. 26, 2024, 8 pages.
Application No. KR10-2020-7018806 , Office Action, Mailed on Dec. 29, 2023, 7 pages.

Examination Report No. 2, Australian Patent Application No. 2018374995, Mailed May 8, 2024; 5 pages, IP Australia.
Notice of Acceptance, Australian Patent Application No. 2018374995, Mailed Sep. 24, 2024, 3 pages, IP Australia.
First Office Action, China Patent Application No. 201880075783.6, Mailed Jul. 17, 2024; 9 pages untranslated/4 pages translated, China National Intellectual Property Administration (CNIPA).
U.S. Appl. No. 17/184,047, "Corrected Notice of Allowability", May 28, 2024, 4 pages.
U.S. Appl. No. 18/168,616, "Corrected Notice of Allowability", Jun. 24, 2024, 5 pages.
U.S. Appl. No. 18/441,936, "Non-Final Office Action", Aug. 28, 2024, 8 pages.
U.S. Appl. No. 18/441,936, "Notice of Allowance", Feb. 26, 2025, 7 pages.
U.S. Appl. No. 18/734,678, "Non-Final Office Action", Feb. 12, 2025, 7 pages.
U.S. Appl. No. 18/734,678, "Notice of Allowance", Apr. 15, 2025, 5 pages.
AU2018374995, "Second Examination Report", May 8, 2024, 5 pages.
BR1120200099279, "Office Action", Jul. 15, 2025, 9 pages.
BR1120200099279, "Office Action", Nov. 26, 2024, 4 pages.
CA3,081,620, "Office Action", Apr. 22, 2025, 3 pages.
CA3080903, "Office Action", Mar. 4, 2025, 4 pages.
CN201880075783.6, "Notice of Decision to Grant", Dec. 11, 2024, 7 pages.
CN201880076771.5, "Office Action", Mar. 11, 2025, 16 pages.
EP18880996.6, "Office Action", Jul. 4, 2025, 4 pages.
EP18880996.6, "Office Action", Nov. 18, 2024, 5 pages.
EP18882550.9, "Intention to Grant", Aug. 7, 2025, 8 pages.
EP25166658.2, "Extended European Search Report", Jul. 22, 2025, 9 pages.
EP18884766.9, "Summons to Attend Oral Proceedings", Aug. 27, 2025, 11 pages.

* cited by examiner

HEPARIN 30000 TO IV
PROTOCOL

5. PHOTOGRAPH
   SYRINGE.

IV COMPOUNDING SYSTEMS AND METHODS

CROSS-REFERENCE TO RELATED APPLICATIONS

This application is a Divisional of U.S. patent application Ser. No. 15/827,336, filed on Nov. 30, 2017, entitled "IV COMPOUNDING SYSTEMS AND METHODS", the disclosure of which is incorporated by reference herein in its entirety.

BACKGROUND OF THE INVENTION

Pharmaceutical compounding is the preparation of medications by the processing or combination of ingredients. Many medications, especially medications administered orally in pill form, are now manufactured in a variety of forms and dosages so that little preparation is needed at a pharmacy, other than placing the proper number of pills in a bottle to fill a doctor's prescription for a particular patient. However, medications for intravenous delivery are routinely compounded, for example in hospital pharmacies. Compounded medications may be patient-specific, or frequently-used medications may be prepared and stocked for later use.

Typically, a physician will prescribe a particular medication or a combination of medications for a specific patient, for intravenous (IV) delivery. The pharmacy receives the prescription and prepares the IV solution with the proper amount of each prescribed medication. The compounded medication is then sent to the hospital floor for administration to the patient.

It is of utmost importance that the correct medications be prepared in the correct proportions, without the introduction of contaminants. Detailed protocols may be developed for the compounder to follow. The number of different protocols may be very large, because there may be a large number of different medications to choose from, in a variety of packages, to be prepared in a number of different ways, in a number of dosages, and to be provided in a number of different delivery vehicles.

Much of the work of compounding may be delegated to workers who are not registered pharmacists, or to robotic machines. Accordingly, meticulous records may be kept of the preparation of each medication, so that the pharmacist can review how each medication was made before it leaves the pharmacy. The records also enable review of the preparation of any particular medication at a later time, should there be any question of its correctness.

BRIEF SUMMARY OF THE INVENTION

According to one aspect, a method of compounding a medication comprises receiving, in a user interface presented on electronic display, a list of a number of workflow types differentiated at least in part by the kind of vehicle in which a completed compounded pharmaceutical is to be delivered, and selecting one of the number of workflow types. The method further comprises receiving, in the user interface, a list of a number of compounding device types, and selecting one of the number of compounding device types. The method further comprises receiving, in the user interface, a presentation of a number of options applicable to compounding a pharmaceutical on the selected device type into the delivery vehicle of the selected workflow type, and selecting one or more of the options. The method further comprises receiving, in the user interface, an automatically constructed workflow for compounding a pharmaceutical into the selected delivery vehicle on the selected device type, in accordance with the selected options, wherein the workflow includes placeholders for information to be determined by a specific pharmaceutical to be compounded according to the constructed workflow, and specifying a particular pharmaceutical to be compounded according to the constructed workflow. The method further comprises receiving, in the user interface an automatically constructed compounding protocol constructed from the constructed workflow by inserting information about the particular pharmaceutical into the constructed workflow. The method further comprises causing the compounding protocol to be transmitted to a compounding device of the selected compounding device type, and compounding the specified pharmaceutical into the delivery vehicle of the selected workflow type in accordance with the compounding protocol. In some embodiments, the specified pharmaceutical may be compounded into a container suitable for intravenous delivery of the specified pharmaceutical, or may be compounded into a container suitable for oral liquid delivery of the specified pharmaceutical.

According to another aspect, a system for pharmaceutical compounding comprises a processor, an electronic display, and memory. The memory holds instructions that, when executed by the processor, cause the system to present on the electronic display a number of workflow types differentiated at least in part by the kind of vehicle in which a completed compounded pharmaceutical is to be delivered, and receive from a user a selection of one of the workflow types. The instructions further cause the system to present on the electronic display a number of options applicable to compounding a pharmaceutical on the selected device type into the delivery vehicle of the selected workflow type, and receive from the user selections of one or more of the options. The instructions further cause the system to automatically construct a workflow for compounding a pharmaceutical into the delivery vehicle of the selected workflow type, in accordance with the selected options. In some embodiments, the instructions further cause the system to present on the electronic display a number of compounding device types, and receive from the user a selection of one of the compounding device types, wherein the workflow is tailored to the selected device type. In some embodiments, the constructed workflow includes placeholders for information to be determined by a specific pharmaceutical to be compounded according to the constructed workflow, and the instructions further cause the system to receive from the user a specification of a particular pharmaceutical to be compounded according to the constructed workflow, automatically construct a compounding protocol from the constructed workflow by inserting information about the particular pharmaceutical into the constructed workflow, and store the compounding protocol in a protocol database. In some embodiments, the system further comprises a compounding assistance device, and the instructions further cause the system to transmit the compounding protocol to the compounding assistance device, wherein the compounding assistance device leads a user of the compounding assistance device through a compounding task according to the compounding protocol, using a series of prompts displayed on a screen of the compounding assistance device. In some embodiments, the system further comprises a compounding robot, and the instructions further cause the system to transmit the compounding protocol to the compounding robot, wherein the compounding robot compounds the particular pharmaceutical into the delivery vehicle of the selected workflow type in accordance with the compounding protocol. In some embodiments, the instructions further cause the system to accept from the user a specification of an instructional message to be inserted into the workflow, and insert the instructional message into the workflow.

According to another aspect, a method of specifying a protocol for pharmaceutical compounding comprises presenting on an electronic display a number of workflow types differentiated at least in part by the kind of vehicle in which a completed compounded pharmaceutical is to be delivered, and receiving, from a user, a selection of one of the workflow types. The method further comprises presenting on the electronic display a number of options applicable to compounding a pharmaceutical into the delivery vehicle of the selected workflow type, and receiving, from the user, selections of one or more of the options. The method further comprises automatically constructing a workflow for compounding a pharmaceutical into the delivery vehicle of the selected workflow type, in accordance with the selected options. In some embodiments, the constructed workflow includes placeholders for information to be determined by a specific pharmaceutical to be compounded according to the constructed workflow, and the method further comprises receiving, from the user, a specification of a particular pharmaceutical to be compounded according to the constructed workflow; automatically constructing a compounding protocol from the constructed workflow by inserting information about the particular pharmaceutical into the constructed workflow; and storing the compounding protocol in a protocol database. In some embodiments, the method further comprises presenting on the electronic display a number of compounding device types, and receiving, from the user, a selection of one of the compounding device types; wherein the workflow is constructed for compounding on the selected device type. In some embodiments, the method further comprises receiving an order for preparation of the particular pharmaceutical, and transmitting the compounding protocol via an electronic network to a compounding device of the selected device type. In some embodiments, the compounding device is a compounding assistance device, and the method further comprises leading a user of the compounding assistance device through a compounding task to compound the particular pharmaceutical into the delivery vehicle of the selected workflow type by displaying a series of prompts on a display of the compounding assistance device. In some embodiments, the method further comprises requiring that the result of at least a portion of the compounding task be approved by a second person other than the user. In some embodiments, the method further comprises transmitting data from the compounding assistance device to the second person at a remote location, and receiving approval from the second person from the remote location. In some embodiments, the compounding device is a compounding robot, and the method further comprises robotically compounding the specified pharmaceutical into the delivery vehicle of the selected workflow type, according to the compounding protocol. In some embodiments, one of the options specifies a technique for documenting a dosage verification of the particular pharmaceutical used in a compounding task. In some embodiments, only options for the technique for documenting the dosage verification are presented that are compatible with the delivery vehicle of the selected workflow type and with any intermediate containers used on the compounding task. In some embodiments, the method further comprises preparing a library of workflows according to a predefined rule set, and the rule set specifies which combinations of delivery vehicle, device type, and options are permitted. In some embodiments, the method further comprises receiving an indication that the constructed workflow is to include steps for including two different pharmaceuticals into the delivery vehicle of the selected workflow type, and including steps in the constructed workflow for compounding the two different pharmaceuticals into the delivery vehicle of the selected workflow type. In some embodiments, the constructed workflow includes placeholders for information to be determined by the two pharmaceuticals to be compounded according to the constructed workflow, and the method further comprises receiving, from the user, specifications of two particular pharmaceuticals to be compounded according to the constructed workflow; automatically constructing a compounding protocol from the constructed workflow by inserting information about the two particular pharmaceuticals into the constructed workflow; and storing the compounding protocol in a protocol database. In some embodiments, the method further comprises adding a premade pharmaceutical formulation to a formulary with an indication that the premade pharmaceutical formulation is premade, constructing a virtual protocol relating to the pharmaceutical in the premade pharmaceutical formulation, receiving an order for preparation of the pharmaceutical in the premade pharmaceutical formulation, and presenting the virtual protocol to the user as an option for filling an order for the particular pharmaceutical. In some embodiments, automatically constructing the workflow comprises including in the workflow a requirement that a result of at least part of a compounding task performed according to the workflow be verified and approved by a second person other than the user. In some embodiments, the method further comprises receiving, from the user, a specification of an instructional message to be inserted into the workflow, wherein automatically constructing the workflow comprises inserting the instructional message into the workflow.

According to another aspect, a user interface for specifying a protocol for pharmaceutical compounding comprises a first user interface screen for display on an electronic display, the first user interface screen presenting a list of compounding workflow types differentiated at least in part by the kind of vehicle in which a completed compounded pharmaceutical is to be delivered, the first user interface screen enabling selection of one of the compounding workflow types. The user interface further comprises a second user interface screen, the second user interface screen reached after selection of a respective one of the compounding workflow types on the first user interface screen, and the second user interface screen presenting a number of options for configuring a workflow for a particular compounding task. The second user interface screen depicts the configured workflow and updates the configured workflow in real time as options are selected on the second user interface screen. The configured workflow is depicted with placeholders for the insertion of ingredients needed for the workflow. In some embodiments, the first user interface screen also presents a list of compounding device types and enables selection of one of the compounding device types, and the second user interface screen is tailored to a particular compounding device type. In some embodiments, the user interface further comprises another user interface screen that enables selection of a stored workflow, enables specification of a particular pharmaceutical to be compounded in accordance with the selected workflow, displays a compounding protocol for compounding the specified pharmaceutical in accordance with the selected workflow, and updates the displayed compounding protocol in real time in accordance with changes in the workflow selection and pharmaceutical specification. In some embodiments, the second user interface screen enables specifying that the workflow is to include steps for compounding two different pharmaceuticals into the specified delivery vehicle, and the user interface further comprises another user interface screen that enables selection of a stored workflow including steps for compounding two different pharmaceuticals into the specified delivery vehicle, enables specification of two particular pharmaceuticals to be compounded in accordance with the selected workflow, displays a compounding protocol for compounding the two specified pharmaceuticals in accordance with the selected workflow, and updates the displayed compounding protocol in real time in accordance with changes in the workflow selection and pharmaceutical specification. According to another aspect, the user interface further comprises a third user interface screen containing fields for entering information about a pharmaceutical to be added to a formulary, the third user interface screen also including a user interface selection for indicating that the pharmaceutical is premade; and a fourth user interface screen enabling assignment of a compounding task, the fourth user interface screen presenting a virtual protocol to the user, the selection of which signals that the drug is premade.

DETAILED DESCRIPTION OF THE INVENTION

Figure 1:
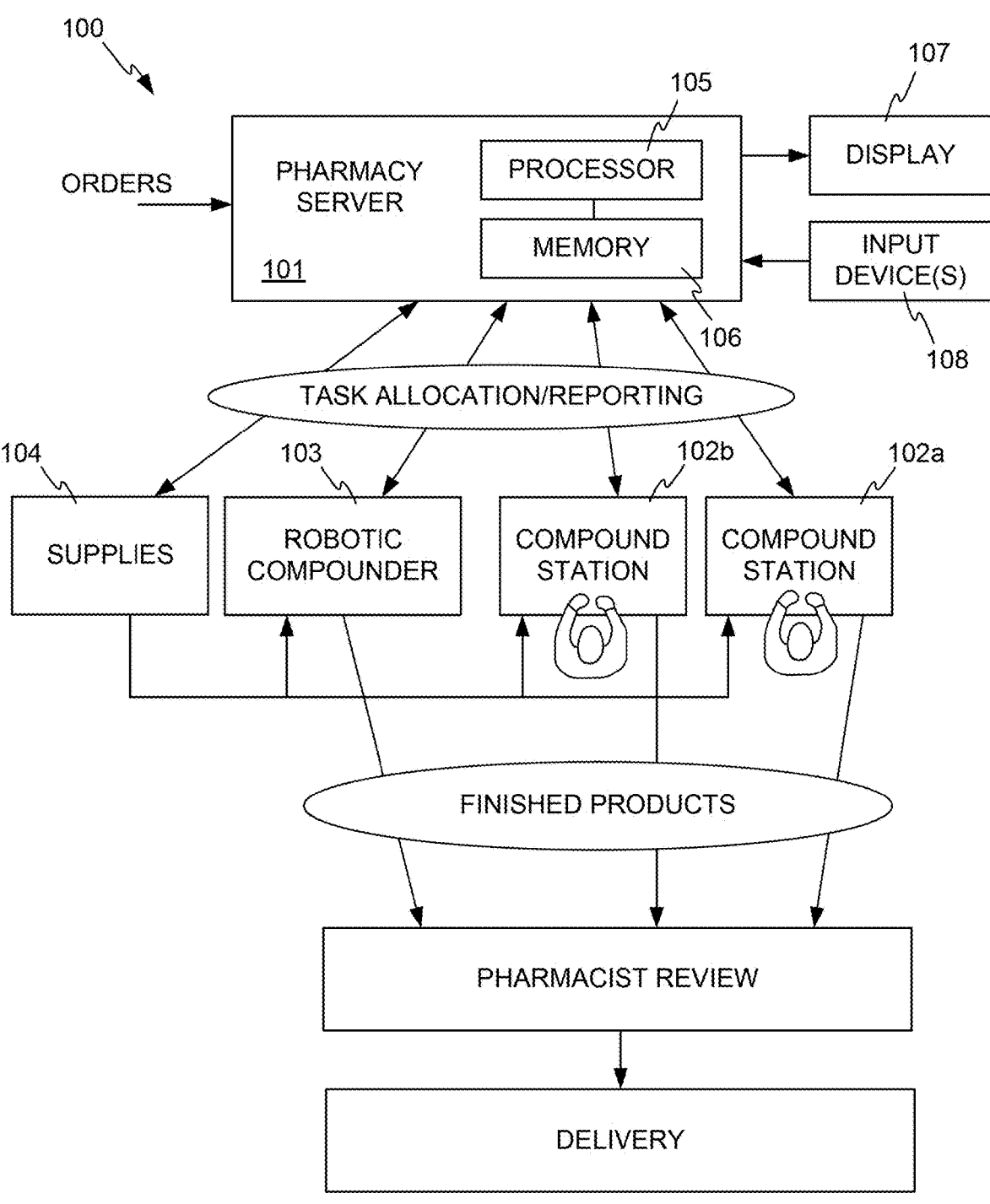
FIG. 1 illustrates a compounding pharmacy in accordance with embodiments of the invention.

FIG. 1 illustrates a compounding pharmacy 100 in accordance with embodiments of the invention. The operation of pharmacy 100 is coordinated by a pharmacy server 101, described in more detail below. Pharmacy server 101 receives orders for compounded medications, for example prescriptions from physicians. Pharmacy server 101 maintains extensive records of orders received, detailed protocols for the compounding of medications, records of the preparation of medications in response to orders, and other items. Pharmacy server 101 also allocates tasks to one or more compounding stations, which may include manual compounding stations such as stations 102a and 102b, and one or more robotic compounders 103. The compounding stations may also report information to pharmacy server 101, for example records of the compounding of each ordered medication.

Pharmacy server 101 includes a processor 105 and memory 106. Memory 106 holds instructions that, when executed by processor 105, cause pharmacy server to perform its functions in accordance with embodiments of the invention. Memory 106 may also hold the records, protocols, and other information collected and generated in the operation of pharmacy 100. For the purposes of this disclosure, the term "memory" encompasses many different kinds of data storage devices and combinations of such devices, for example dynamic memory, static memory, volatile memory, nonvolatile memory, and mass storage such as magnetic or optical disk storage or tape storage.

While pharmacy server 101 is shown as a single block in FIG. 1 and could be a single, stand-alone computer system having memory 106 and one or more processors 105, other implementations are possible. For example, pharmacy server may be implemented using a number of interconnected computers, either co-located or in multiple locations. In particular, pharmacy server 101 may be implemented as a "cloud" service, in which the functions of pharmacy server 101 may be performed by different processors at different times, and memory 106 may be distributed as well. Pharmacy server 101 presents information to a user via a user interface shown on an electronic display 107, and may receive inputs from the user via any input device or devices 108, for example a keyboard, mouse, other pointing device, or other input devices or combinations of input devices.

Working materials are supplied to the compounding stations from a supply store 104. Pharmacy server 101 may maintain an inventory of the materials in supply store 104, and may track the movements of medications and supplies within pharmacy 100.

Finished products are reviewed by the pharmacist and delivered from pharmacy 100 to their points of use, for example patient rooms for administration by a nurse to a patient. It will be understood that the above description is highly generalized, and that a working compounding pharmacy may have many other systems and facilities.

Figure 2:
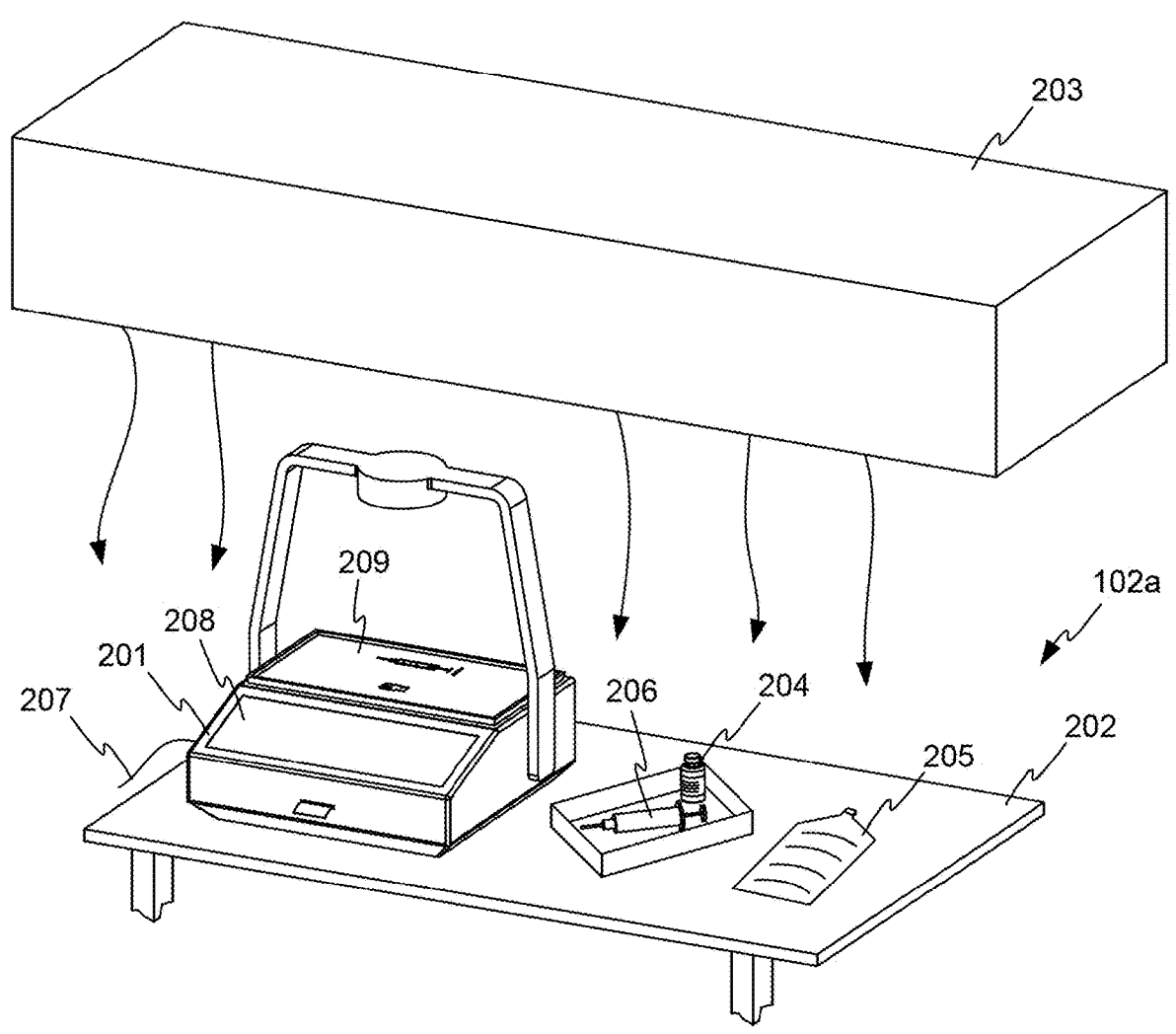
FIG. 2 illustrates a manual compounding station in accordance with embodiments of the invention.

FIG. 2 illustrates a manual compounding station 102a in accordance with embodiments of the invention. Compounding station 102a includes a compounding assistance device 201 on a surface 202. For the purposes of this disclosure, a compounding assistance device is an electromechanical device having features and capabilities, examples of which are described below, for facilitating the performance of a compounding task by a human operator. Compounding assistance device 201 may be placed under a laminar flow hood 203, which flows filtered air over compounding assistance device 201 and surface 202, to help avoid contamination of the materials being worked on, and for protection of the user of compounding station 102a.

In the example shown, compounding station 102a has received supplies for a simple compounding task. A medication supplied in a vial 204 is to be added to an IV drip bag 205. A syringe 206 may be used to accomplish the transfer.

Compounding assistance device 201 has several features and capabilities that will assist the compounder in properly preparing the formulation in IV drip bag 205, and in thoroughly documenting the process. Compounding assistance device 201 has a network connection 207 to pharmacy server 101, though which compounding assistance device 201 may receive instructions from pharmacy server 101 describing the steps required to perform the compounding task.

For the purposes of this disclosure, a protocol is a list of ingredients and containers and a reference to the processing workflow to produce a specific IV medication. A workflow is a generic set of steps, specified independent of the particular medication and dosage of the specific compounding task. One workflow can describe the generic steps required for a kind of compounding task. Many different protocols may reference the workflow, for specific medications and amounts. For example, a particular workflow may describe the steps needed to draw medication from a vial and add it to an IV drip bag. Multiple protocols can then reference that workflow for placing a specific dosage of a specific medication in the drip bag. This point will be explained further below.

Compounding assistance device 201 includes a display screen 208 on which instructions to the user may be presented or through which the user may input information. For example, display screen 208 may be a touchscreen display, sensitive to touch and able to distinguish the location of a touch. Compounding assistance device 201 also includes a tray 209 which provides a carrier for holding items while they are weighed or photographed, as is described in more detail below.

Figure 3:
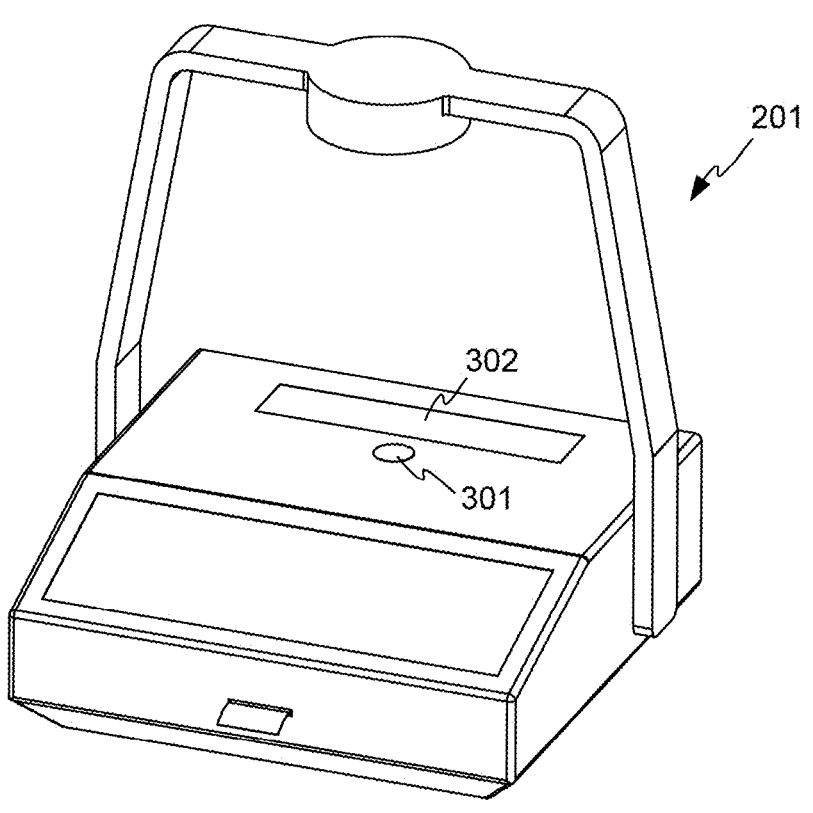
FIG. 3 shows a compounding assistance device, in accordance with embodiments of the invention.

FIG. 3 shows compounding assistance device 201, with tray 209 removed, in accordance with embodiments of the invention. Visible in FIG. 3 is a weight sensor 301, for example a load cell, for weighing tray 209 and its contents. Also visible is a light source 302. Light source 302 may be, for example, an infrared light panel, illuminating a portion of tray 209 from below with infrared light.

Figure 4:
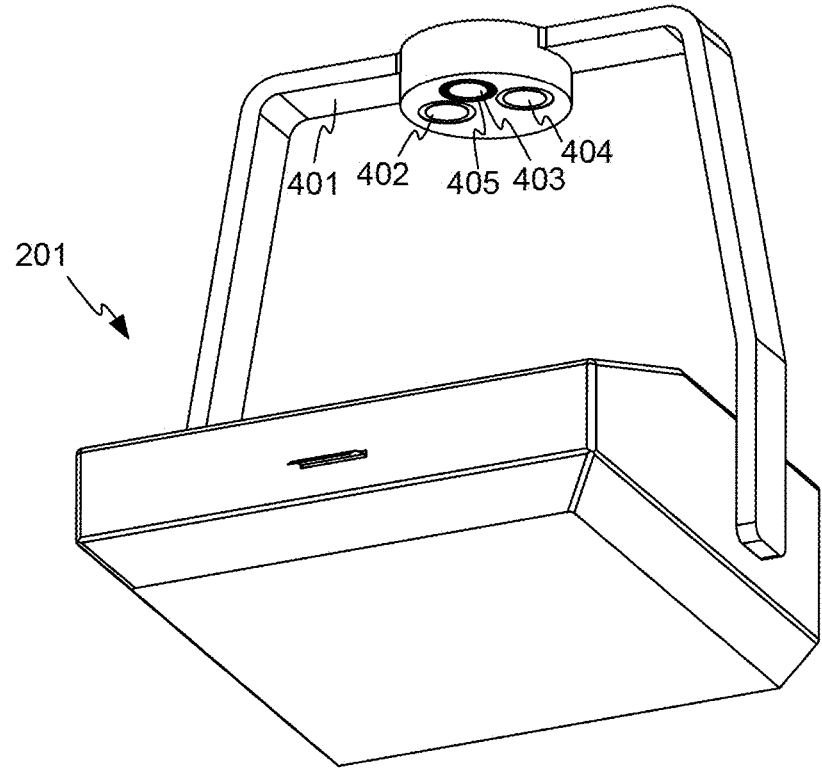
FIG. 4 shows a lower oblique view of the compounding assistance device of FIG. 3, in accordance with embodiments of the invention.

FIG. 4 shows a lower oblique view of compounding assistance device 201, in accordance with embodiments of the invention. A gantry 401 spans tray 209. Positioned on gantry 401 are a bar code scanner 402, a visible light camera 403, and an infrared camera 404. Visible light camera 403 may further include one or more light sources 405 for illuminating at least a portion of tray 209 from above. Light sources 405 may be, for example, one or more white-light light emitting diodes (LEDs) surrounding visible light camera 403, or another kind of light source. For the purposes of this disclosure, light is "visible" if it includes light wavelengths between about 400 and 700 nanometers. Light is "white" if it includes enough wavelengths in the visible range to enable reasonably complete color recognition.

The area above tray 209 may be called a viewing area for items to be photographed by infrared camera 404 or visible light camera 403, or scanned by bar code scanner 402. In other embodiments, an item may not necessarily be lit from below and photographed from above. For example, in a compounding robot, a robotic mechanism may hold an item to be photographed in the field of view of a camera in any orientation. For example, an item may be photographed from below, or horizontally.

Bar code scanner 402 is positioned to read bar codes on items held in the viewing area between tray 209 and bar code scanner 402. Visible light camera 403 and infrared camera 404 are position to take photographs of items on tray 209.

During compounding of a medication one or more of weight sensor 301, bar code scanner 402, visible light camera 403, and infrared camera 404 can be used to provide documentation of how the medication was compounded, and to avoid errors.

For example, to perform the compounding task illustrated in FIG. 2, pharmacy server 101 transmits detailed sequential instructions to compounding assistance device 201, which then leads the user through the steps required to formulate the specific medication in the specific dose required, for delivery in the specific delivery vehicle. In this example, the task may involve transferring 30000 units of Heparin (a common anticoagulant) from a vial containing 5000 units/ml of Heparin in solution, to an IV drip bag. The volume of solution required for transfer is therefore 6 ml. Vial 204 and IV drip bag 205 have been supplied to compounding station 102*a*, along with syringe 206, which will be needed to make the transfer.

Figure 5:
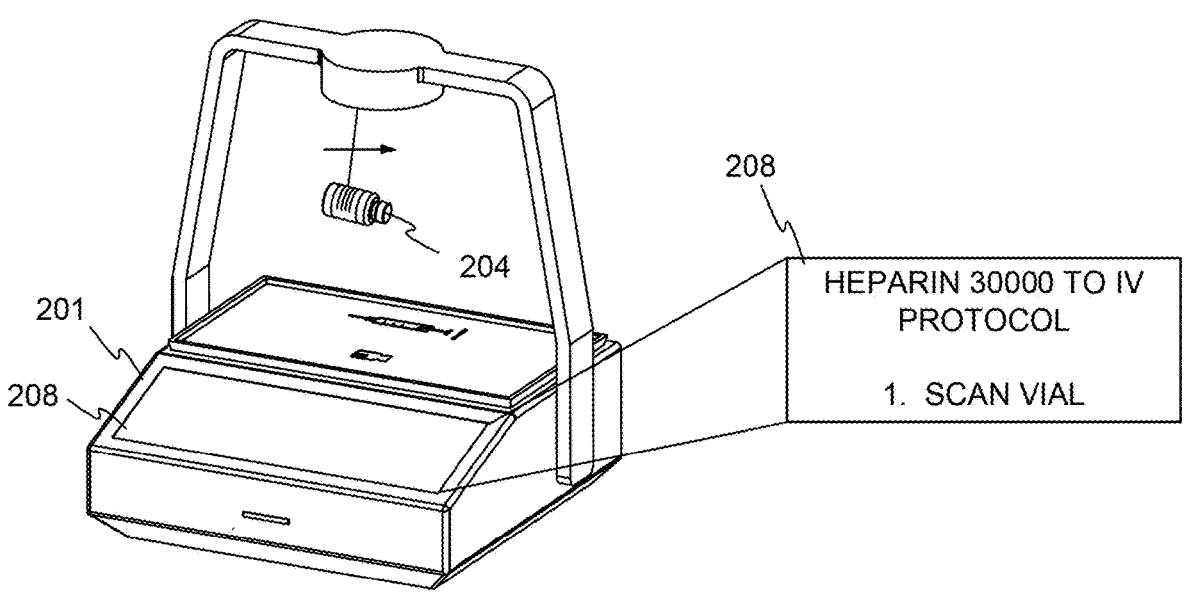
FIG. 5 illustrates bar code scanning by the compounding assistance device of FIG. 3, in accordance with embodiments of the invention.

First, compounding assistance device 201 requires that the user present vial 204 to bar code scanner 402, so that the identifying bar code on vial 204 can be read, and the system can verify that the correct vial with the correct concentration has been provided. If not, then an error message is generated and the compounding task is stopped. The scanning process is illustrated in FIG. 5, along with an example prompt shown on screen 208. Compounding assistance device 201 may automatically recognize that the barcode has been detected, and may move to the next step. Alternatively, an acknowledgment from the user may be required, in this and other steps.

Figure 6:
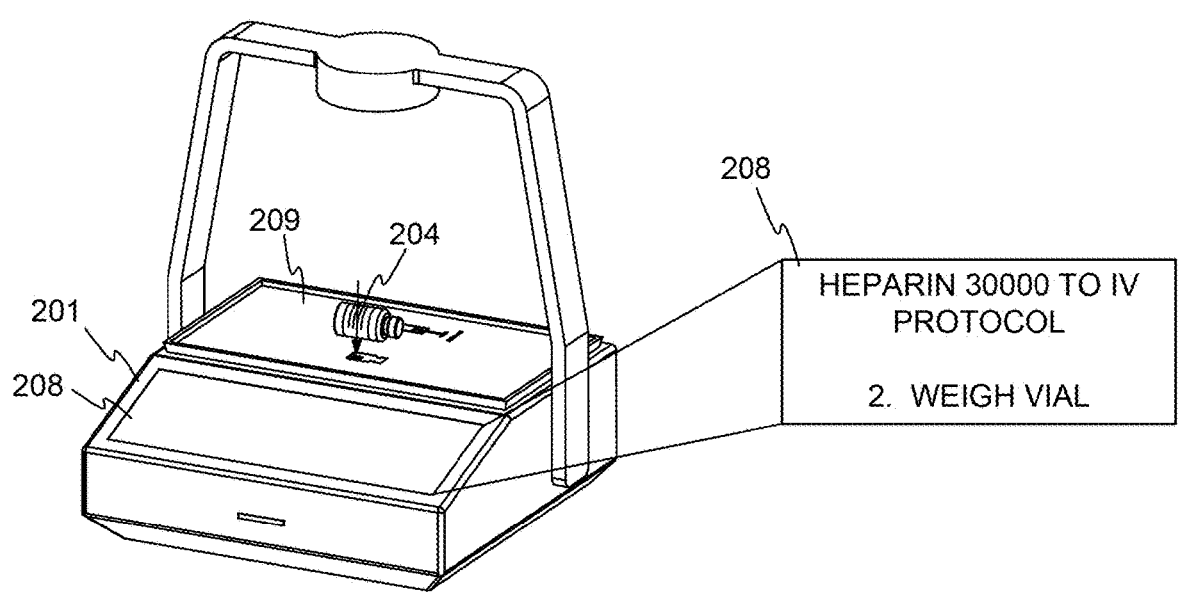
FIG. 6 illustrates a step in a compounding process, in accordance with embodiments of the invention.

FIG. 6 illustrates a second step in the compounding process, in which an initial weight of vial 204 is collected. For this purpose, vial 204 is placed on tray 209. Tray 209 may include an icon 601 indicating where vial 204 should be placed, and may also include mechanical features for aiding in proper placement of vial 204. For example, a gently V-shaped trough may be formed into tray 209. Compounding assistance device 201 may automatically recognize the weight of vial 204 on tray 209, record the weight, and move to then next step of the compounding process.

In some embodiments, vial 204 may also be photographed while on tray 209 using visible light camera 403, using ambient light, light from light sources 405, or a combination thereof.

Figure 7:
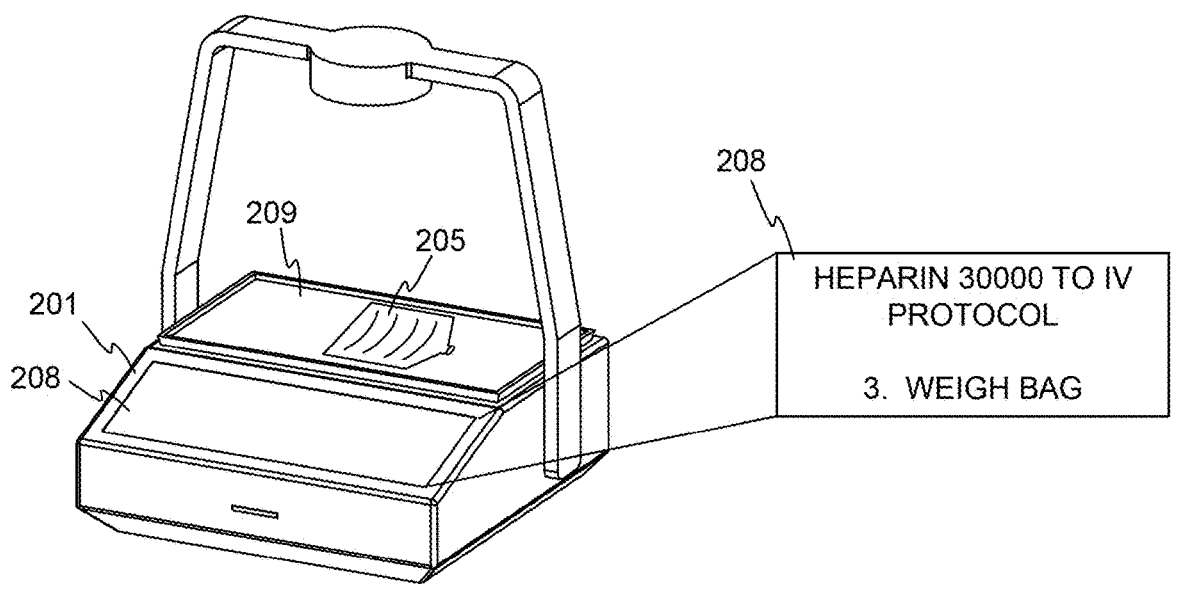
FIG. 7 illustrates another step in the compounding process, in accordance with embodiments of the invention.

FIG. 7 illustrates a third step, in which an initial weight of IV bag 205 is collected. Compounding assistance device 201 may then prompt the user to draw the correct amount (6 ml) of solution from vial 204 into syringe 206.

Figure 8:
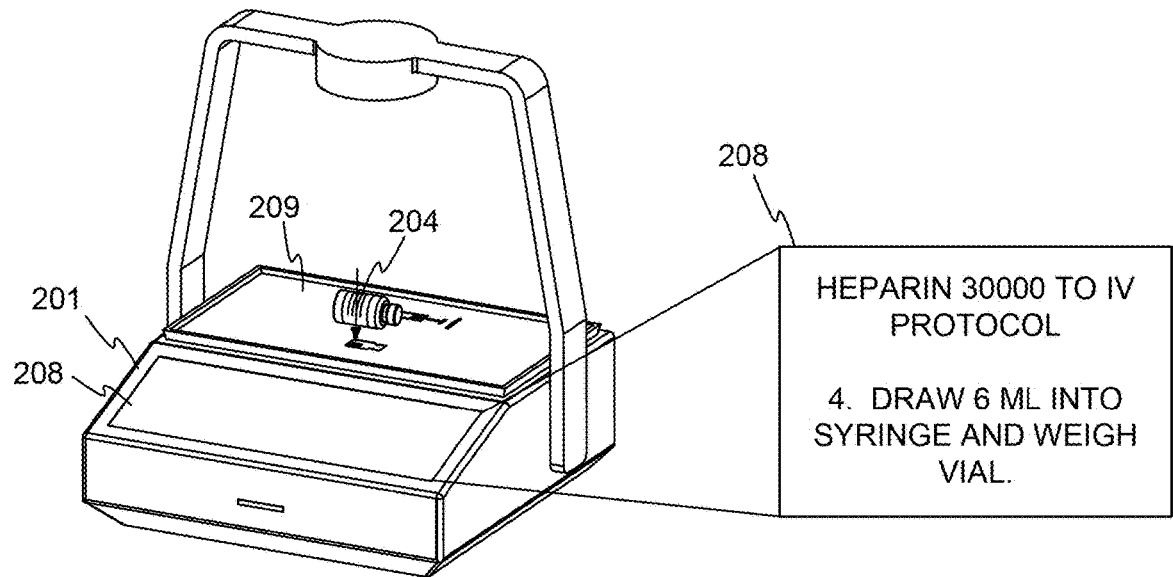
FIG. 8 illustrates another step in the compounding process, in accordance with embodiments of the invention.

FIG. 8 illustrates a fourth step, in which an after-drawn weight of vial 204 is taken, in a manner similar to the taking of the initial vial weight shown in FIG. 6. The system can compare the two weights of vial 204 to calculate the amount of solution drawn from vial 204, for recordkeeping and for verification that the proper amount of solution was drawn.

Figure 9:
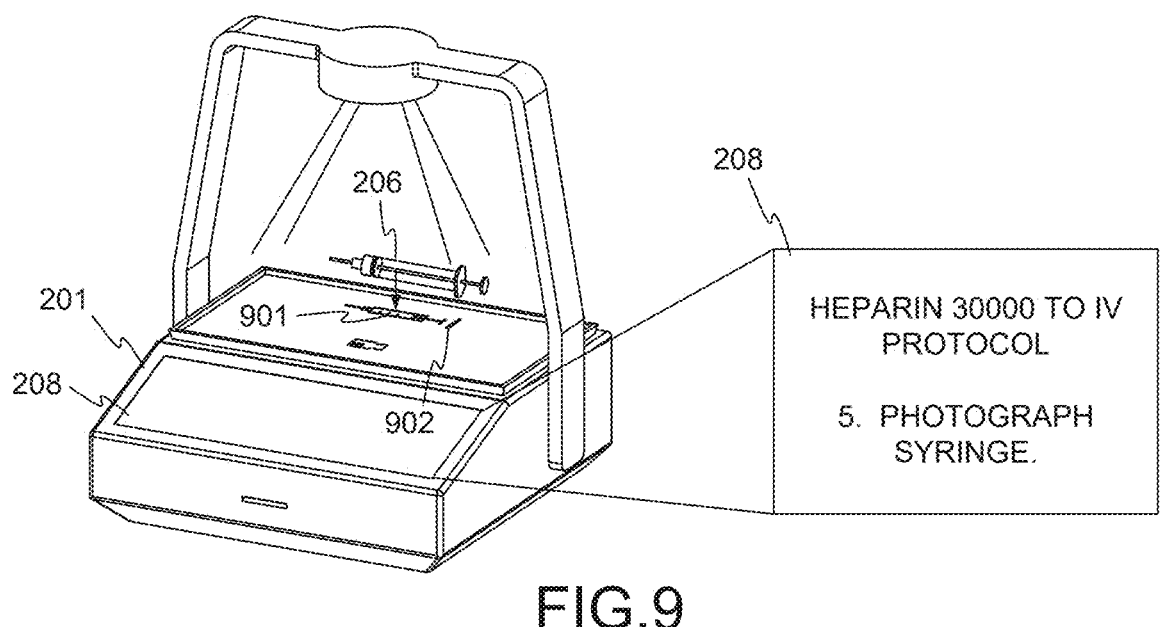
FIG. 9 illustrates another step in the compounding process, in accordance with embodiments of the invention.

FIG. 9 illustrates a fifth step, in which the filled syringe is photographed. For this purpose, tray 209 may include an icon 901 for placement of syringe 206, and may include mechanical features facilitating correct placement and alignment of syringe 206 on tray 209, for example a V-shaped trough, or a groove 902 shaped and sized to receive an edge of the barrel flange of syringe 206. Other fiducial marks may be present as well.

Figure 10:
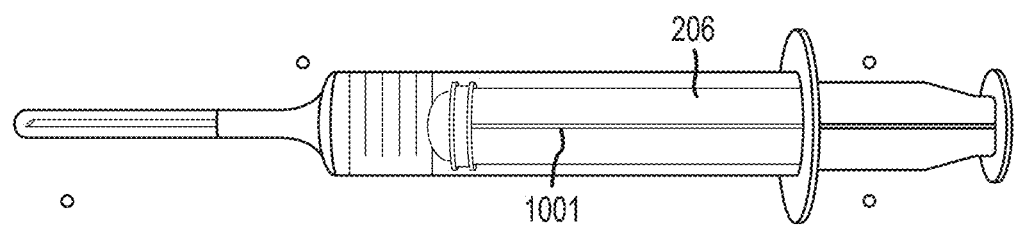
FIG. 10 shows a photograph as may be taken using a visible light camera, in accordance with embodiments of the invention.

Syringe 206 may be photographed using visible light camera 403, but is preferably photographed using infrared camera 404. FIG. 10 shows a photograph as may be taken using visible light camera 403. (Visible light camera 403 preferably has a field of view larger than shown in FIG. 10, but syringe 206 has been isolated from the larger view for ease of explanation.) While syringe 206 is readily visible in the photograph of FIG. 10, the photograph has been affected by glare spot 1001, and may have been affected by ambient light sources that are not under the control of compounding assistance device 201.

Figure 11:
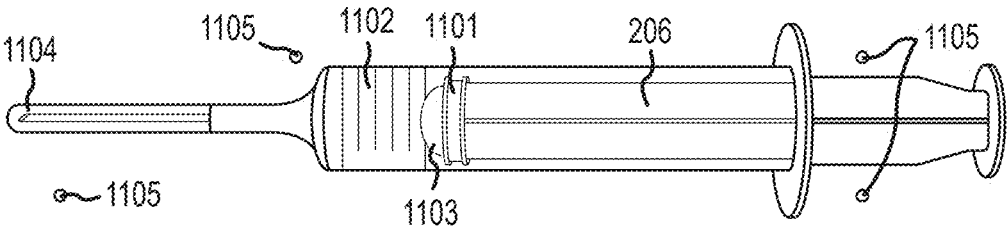
FIG. 11 shows a photograph of a syringe as may be taken using an infrared camera, in accordance with embodiments of the invention.

FIG. 11 shows a photograph of syringe 206 as may be taken using infrared camera 404. Tray 209 is not opaque to infrared radiation, so syringe 206 is backlit by infrared light source 302. For example, tray 209 may be substantially transparent to infrared radiation, or may be translucent. In some embodiments, tray 209 may be made of polycarbonate or another suitable polymer or blend of polymers. Infrared camera 404 may have a wavelength-selective optical filter that passes infrared light to camera 404, but blocks the visible spectrum. Thus, glare spots formed from visible light are excluded from the photograph of FIG. 11, resulting in greater clarity of features of syringe 206.

Whichever kind of camera is used, compounding assistance device 201 can automatically analyze the resulting photograph for any of a number of purposes. For example (referring to FIG. 11), the position of the plunger 1101 of syringe 206 may be automatically recognized, and the amount of drawn liquid 1102 calculated based on the known dimensions of syringe 206. In some embodiments, bubbles such as bubble 1103 may be detected and flagged if they are large enough to significantly affect the dose of medication being prepared. In some cases, the weight of syringe 206 before and after drawing liquid from vial 204 may be used to verify that the correct amount of liquid was placed into syringe 206. In that case, compounding assistance device 201 may also photograph syringe 206 at each weighing and analyze the photographs to detect whether syringe cap 1104 may have been mistakenly included in one weighing but not another. Fiducial marks 1105 on tray 209 are placed in known positions, and may be detected in the photograph and used to calibrate distances in the photograph.

Figure 12:
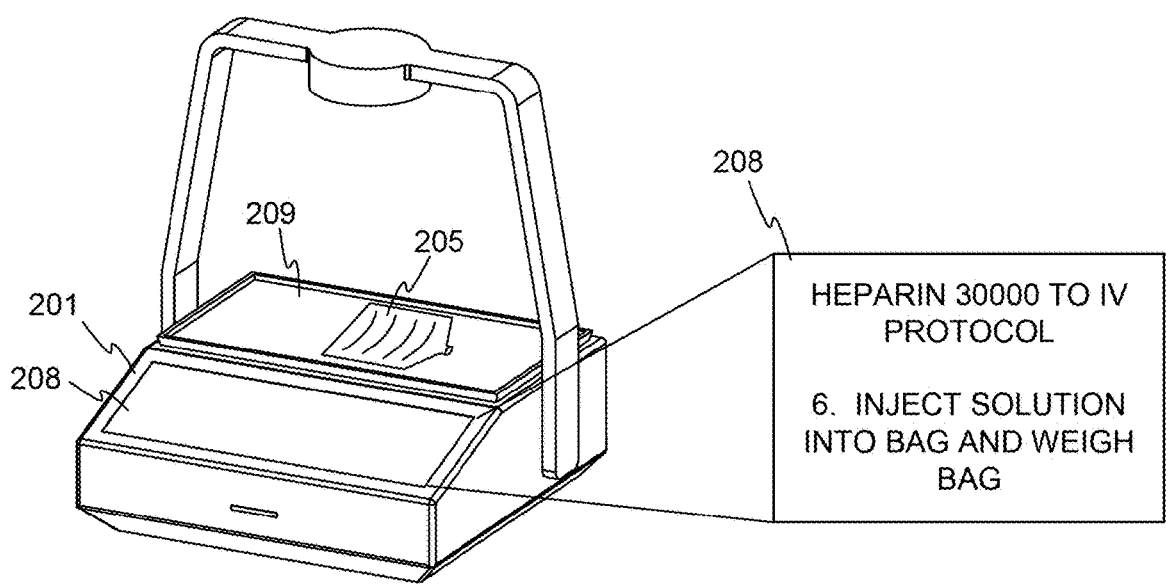
FIG. 12 illustrates another step in the compounding process, in accordance with embodiments of the invention.

FIG. 12 illustrates a sixth step, in which IV bag 205 is re-weighed after addition of solution from syringe 206. Compounding assistance device 201 can compare the before and after weights of bag 205 to verify that the correct amount of Heparin solution was placed into bag 205.

Figure 13:
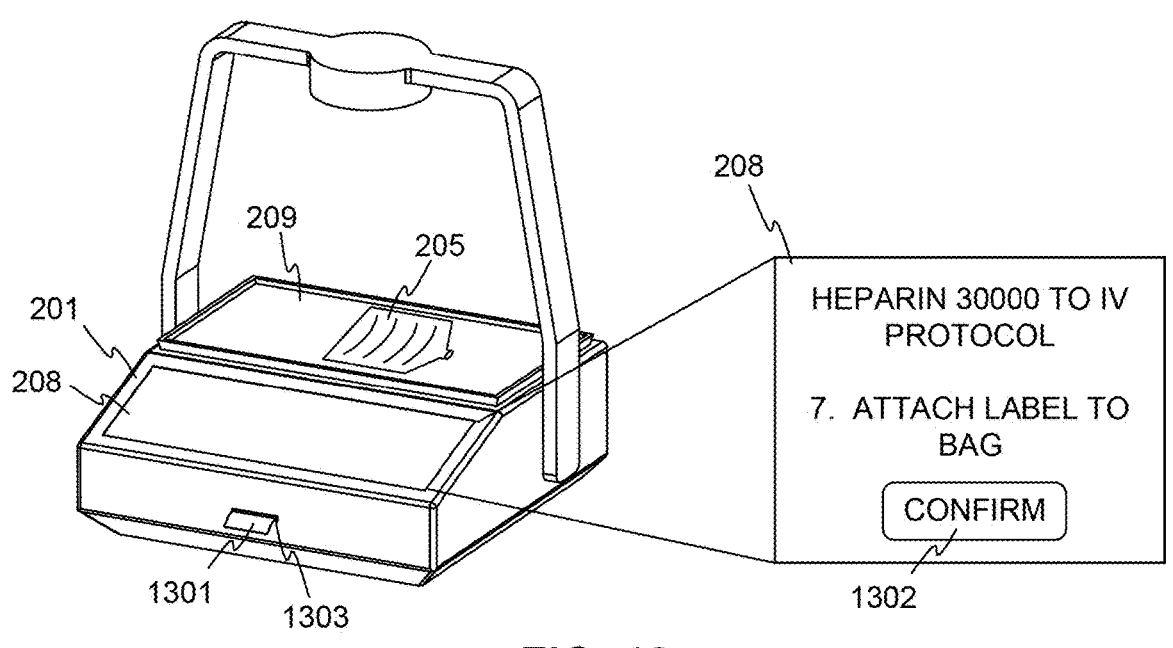
FIG. 13 illustrates another step in the compounding process, in accordance with embodiments of the invention.

FIG. 13 illustrates a seventh step, in which (presuming all of the checks in the system have verified that the compounding process was done correctly) compounding assistance device 201 prints a label 1301 using label printer 1303, to be placed on bag 205, and the user is prompted to adhere label 1301 to bag 205. The finished medication can then be delivered to its point of use, and any consumable items disposed of, for example syringe 206. The user may be asked to confirm 1302 that label 1301 has been affixed, using display 208. In some embodiments, a final photograph of completed bag 205 may be taken for pharmacist review.

The compounding process described above is but one example, and many different compounding workflows may be implemented that have different steps, that use different medication containers, that collect different or additional information for process verification, or that differ in other ways from the example shown.

While the above example was shown in the context of compounding workstation 102*a*, a similar process may be followed for compounding using a robotic compounder such as robotic compounder 103 shown in FIG. 1. A robotic compounder is a machine, usually enclosed, that uses a robotic mechanism to handle vials, syringes, bags, and the like to prepare compounded medications. A robotic compounder may include a scale, one or more cameras, agitation devices, disposal ports, material and supply loading windows, and a delivery window for delivering a finished medication. Robotic compounders are not subject to human error in the compounding process, but include various weight and photographic checks on their work to guard against improper loading of materials, mechanical malfunctions, programming errors, and the like.

Whether compounding is done manually or robotically, the data collected during the compounding process is stored, for example on pharmacy server 101, and can be reviewed by the responsible pharmacist. For example, the pharmacist can verify that the correct kind of vial containing the correct medication was identified by the barcode scan. The dosage can be verified by looking at the photograph of the syringe, the before and after weights of the vial, the before and after weights of the bag, or any combination of these or other data. Any digital photographs taken during the compounding process may be made available for inspection by the pharmacist. For example, the pharmacist may look at a photograph such as the photograph of FIG. 11 to determine whether excessive bubbles may have been included in the liquid drawn into syringe 206.

Upon completion of the compounding task, pharmacy server 101 may assign another compounding task to compounding station 102a, and download another protocol to compounding assistance device 201 in accordance with the new task.

With some of the steps of FIGS. 5-13 expanded, a workflow describing the above example may be listed as:

1. scan barcode of vial containing pharmaceutical;
2. place vial containing pharmaceutical on tray;
3. weigh vial containing pharmaceutical;
4. place bag containing diluent on tray;
5. weigh bag containing diluent;
6. draw pharmaceutical solution into syringe;
7. place vial containing remaining pharmaceutical on tray;
8. re-weigh vial containing remaining pharmaceutical;
9. place filled syringe containing pharmaceutical on tray;
10. photograph filled syringe containing pharmaceutical;
11. inject pharmaceutical from syringe into bag containing diluent;
12. place bag on tray;
13. weigh bag; and
14. affix label to completed bag.

This workflow is specific to placing a pharmaceutical from a vial into an IV bag containing a diluent using a syringe, and using the weight of the vial and a photograph of the syringe as checks on the process. However, the workflow is generic as to the particular drug being transferred, the dosage, the diluent in the bag, and the sizes of the vial and syringe used. For example, the same workflow may be used to dispense a different dosage of Heparin into an IV bag containing a different diluent using a different size of syringe, or to dispense a different drug into an IV bag using the same size of syringe. Each of the different drugs, dosages, diluents, and container sizes would follow a different protocol implemented using the same workflow.

For example, the protocol corresponding to the above example may specify that Heparin is to be dispensed, in a bag containing D5W as a diluent. The workflow can be applied to the protocol and viewed as follows:

1. scan barcode of vial containing Heparin;
2. place vial containing Heparin on tray;
3. weigh vial containing Heparin;
4. place bag containing D5W on tray;
5. weigh bag containing D5W;
6. draw Heparin into syringe;
7. place vial containing remaining Heparin on tray;
8. re-weigh vial containing remaining Heparin;
9. place filled syringe containing Heparin on tray;
10. photograph filled syringe containing Heparin;
11. inject Heparin from syringe into bag containing D5W;
12. place bag on tray;
13. weigh bag; and
14. affix label to completed bag.

Within this protocol, the instructions from pharmacy server 101 to compounding assistance device 201 may include information such as the specific gravity of the 5000 units/ml Heparin solution in the vial, so that compounding assist device 201 can calculate the volume of solution drawn from the vial and placed in the bag based on the before and after weights of the vial and bag.

It will also be recognized that the example compounding task above could be accomplished using a different workflow. For example, rather than using a photograph of the syringe to verify that the correct amount of solution was drawn into the syringe, a different workflow could use before and after weights of the syringe for this purpose. In highly critical situations, a workflow could be designed that does both photographic and weight checks. For example multiple checks may be used in the dispensing of a controlled substance where detection of diversion is especially important, or in pediatric practice where dose accuracy is especially important.

Other workflows may lay out the generic steps for reconstituting and compounding medications received in powdered form, for medications to be delivered in a syringe for direct injection, or for other scenarios. More complex workflows may be designed for compounding multiple medications, for example placing multiple medications in a single IV drip bag.

For each workflow, a number of protocols may use the workflow with particular medications in particular doses. Previously, the preparation of compounding instructions was a laborious task, and was started anew for every medication, dosage, and delivery combination. In accordance with embodiments of the invention, the system facilitates the preparation of protocols and workflows, and in accordance with different delivery containers, verification techniques, and other parameters.

Figure 14:
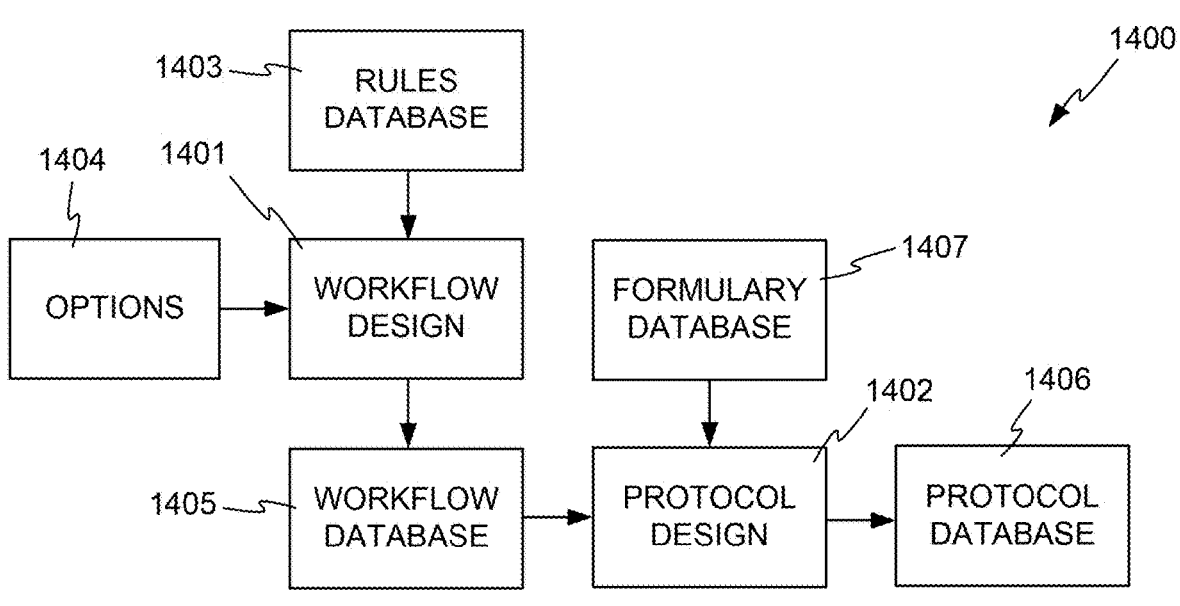
FIG. 14 illustrates a block diagram of a system in accordance with embodiments of the invention, for developing workflows and protocols for pharmaceutical compounding.

FIG. 14 illustrates a block diagram of a system 1400 in accordance with embodiments of the invention, for developing workflows and protocols for pharmaceutical compounding. The system includes modules for workflow design 1401 and protocol design 1402, each accepting inputs from a user and from one or more databases.

For example, workflow design module 1401 accepts workflow templates from rules database 1403 and specifications of one or more options 1404 from a user of the system. Individual designed workflows are stored in workflow database 1405, and become inputs to protocol design module 1402. Finished protocols are stored in protocol database 1406. A list of pharmaceuticals available for compounding is kept in a formulary database 1407.

Figure 15:
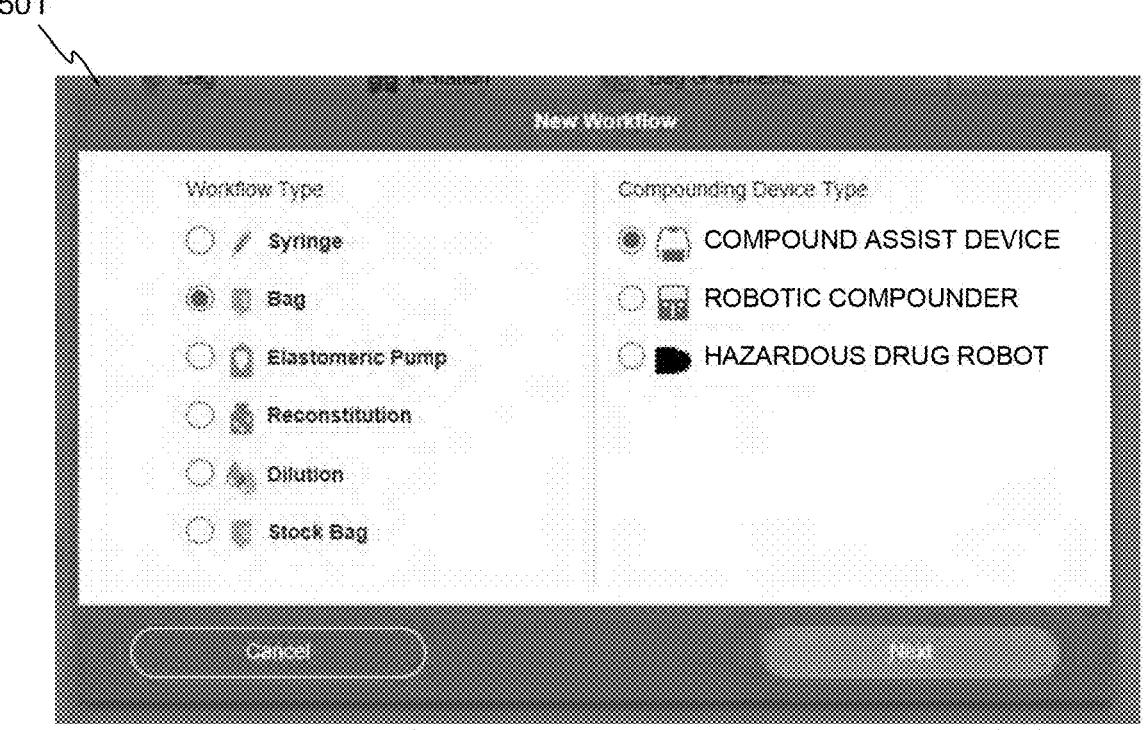
FIG. 15 illustrates a first user interface screen of the workflow design module of FIG. 14, in accordance with embodiments of the invention.

FIG. 15 illustrates a first user interface screen 1501 of workflow design module 1401, in accordance with embodiments of the invention. Screen 1501 presents the user with number of workflow types differentiated by the kind of vehicle in which a completed compounded pharmaceutical is to be delivered. For example, the compounded pharmaceutical may be delivered in a bag, as described above, or in a syringe or elastomeric pump. In other types, the pharmaceutical may be reconstituted in its existing container or may be diluted in its existing container.

Screen 1501 also requests a specification of the type of device on which the compounding will be performed, for example a compounding assistance device such as compounding assistance device 201, a robotic compounder, or a robotic compounder specifically configured for handling dangerous drugs such as cancer treatment drugs. Other workflow or device types may be envisioned.

In example screen 1501, the user has selected to design a workflow for compounding a pharmaceutical to be delivered in an IV bag, on a compounding assistance device. Selection of items from a user interface in embodiments of the invention may be accomplished by any suitable selection mechanism, for example a click with a cursor on a displayed selection, a touch of a finger or stylus on a touchscreen display, a sequence of keystrokes performed on a keyboard, or another selection mechanism.

Figure 16:
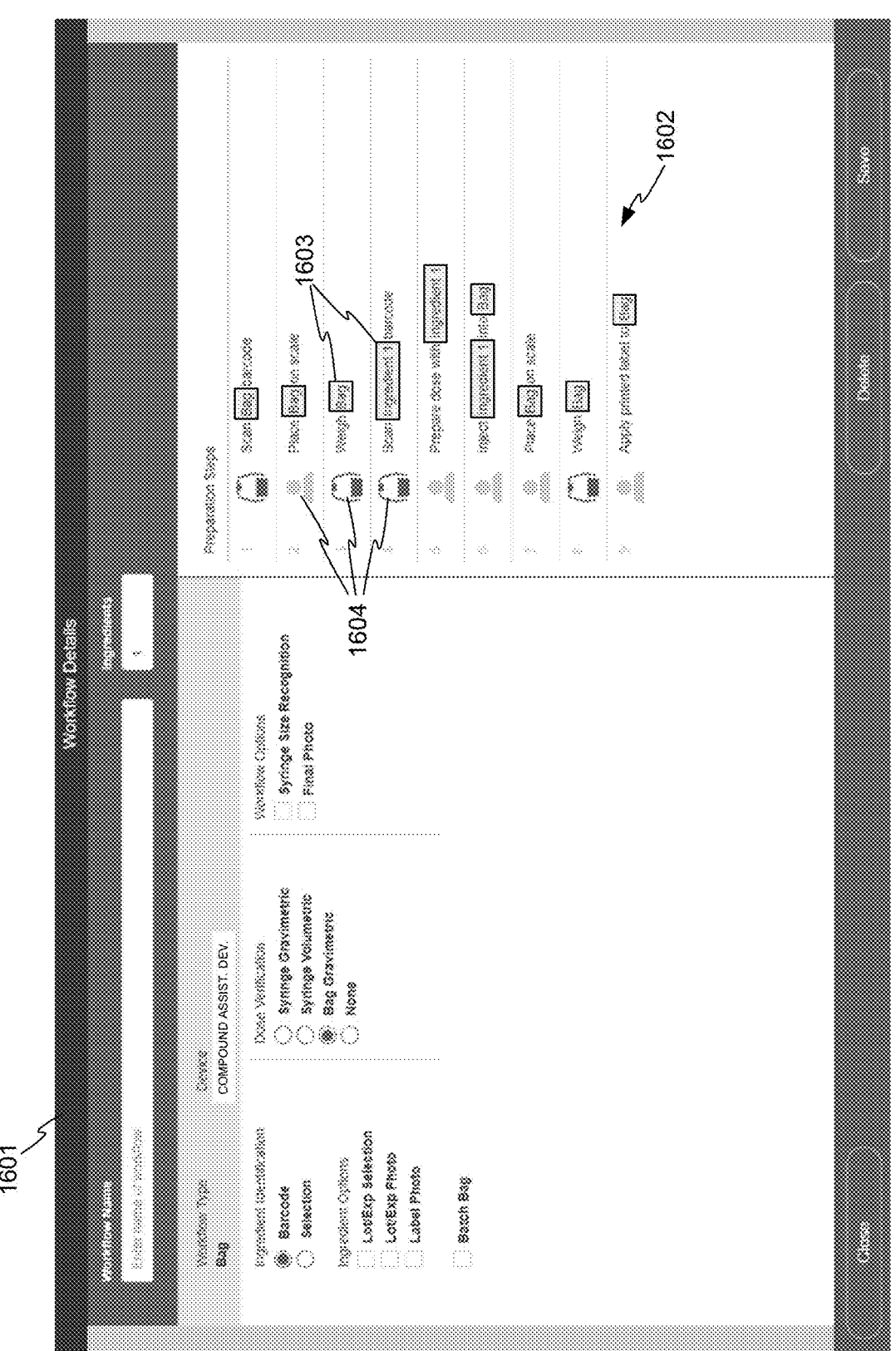
FIG. 16 illustrates a second user interface screen, in accordance with embodiments of the invention.

FIG. 16 illustrates a second user interface screen 1601, in accordance with embodiments of the invention. Screen 1601 may be presented, for example, after the user clicks "Next" on screen 1501. Because it was specified on screen 1501 that the pharmaceutical compounded according to the workflow being designed will be delivered in a bag, the system automatically presents options for bag preparation on screen 1601.

The user can select from a number of options for the workflow. For example, under the heading "Ingredient Identification", the user has specified that barcodes should be scanned from the vial holding the drug to be transferred to the bag and from the bag itself. Alternatively, the user could specify that the items need only be selected from an on-screen list using a computer pointing device to select from a menu, for example.

Under "Dose Verification", the user has specified that the bag should be weighed before and after the transfer of the drug into the bag, for verification that the correct amount of drug was transferred. Alternative verification techniques include weighing the syringe used in the transfer empty and full, or analyzing a photograph of the filled syringe. In some non-critical cases, no verification technique may be indicated. In other embodiments, it may be possible to specify redundant techniques for dose verification.

Other options may be specified as well, for example whether the size of the syringe should be automatically determined, and whether a final photograph of the completed bag should be taken and stored. Other documentation may be specified. For example, a photograph of the vial of the drug being transferred may be required, or the compounder may be required to enter information about the expiration date or lot number of the drug being transferred. Other options may be envisioned.

In some cases, for example in the case of a particularly critical drug or dose size, an in-workflow review may be specified, in which a second person is called to review the work of the first and must enter their credentials for the preparation to be approved. The second person may be the pharmacist, a pharmacy technician, or another qualified person. In some embodiments, the review may be conducted remotely, with the second person viewing photographs, weight data, or other information gathered in the process of compounding the medication. For example, the second person may be located outside the sterile area of the pharmacy, in another part of the hospital, or in any other location worldwide with access to the information.

The options may be selected according to any suitable criteria, for example, the criticality of the medication being compounded, pharmacist preference for certain verification techniques, or other criteria.

As the options are selected, the resulting workflow 1602 may be displayed and updated in real time. Workflow 1602 has placeholders 1603 for the insertion of specific ingredients at the protocol design stage. The individual steps of the workflow may be labeled 1604 to conveniently show which are performed by the compounding assistance device (steps 1, 3, 4, and 8 in this example) and which are performed by the operator of the compounding assistance device (steps 2, 5-7, and 9 in this example).

Figure 17:
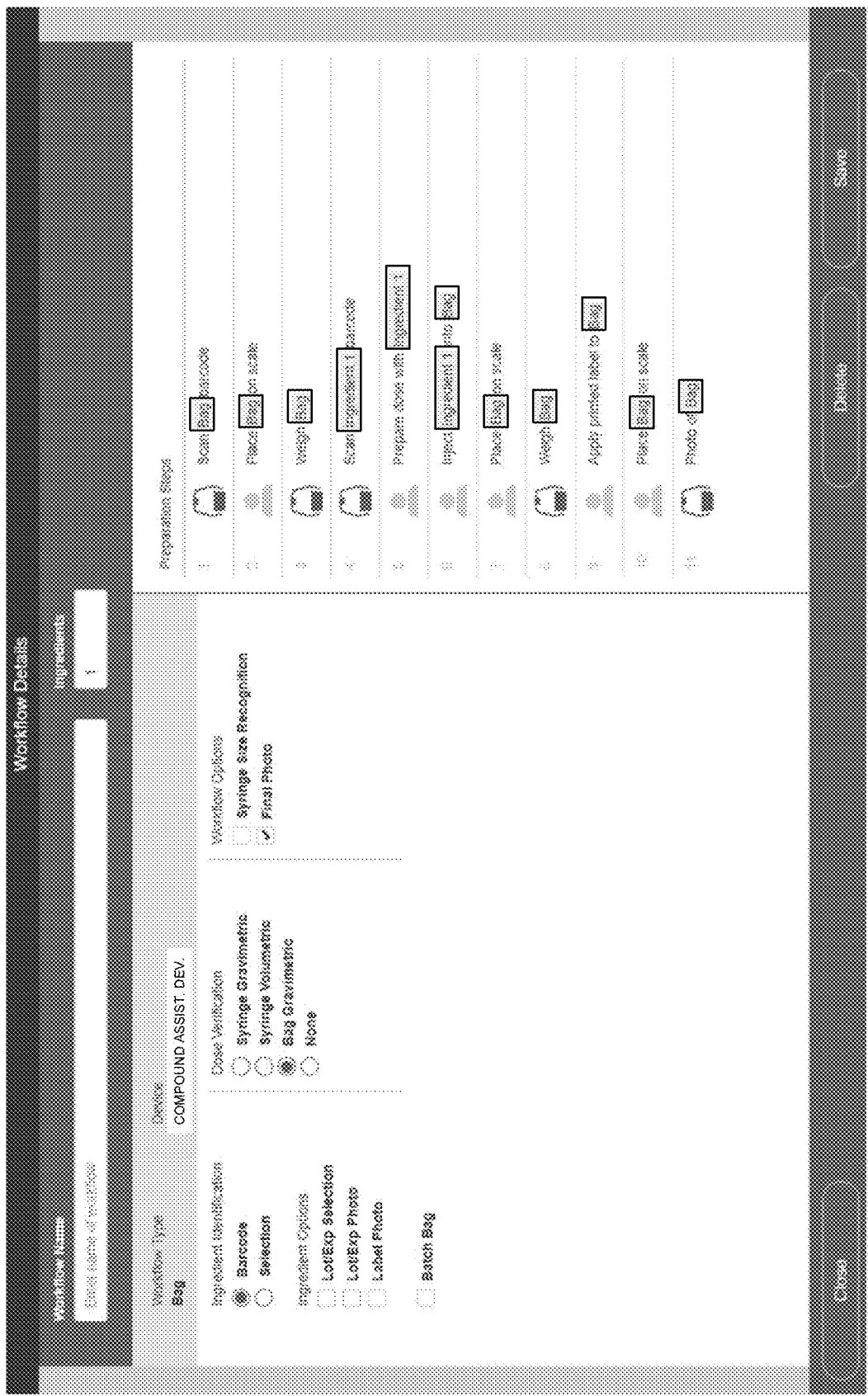
FIG. 17 shows the effect on the screen of FIG. 16 of the selection of a different compounding option, in accordance with embodiments of the invention.

FIG. 17 shows the effect on screen 1601 of the selection of a different option—in this case the specification that a final photograph is to be taken of the finished IV bag once the compounding workflow is completed. As can be seen in FIG. 17, steps 10 and 11 have been automatically added to the workflow, in which the user will be instructed to place the bag on the compounding assistance device (step 10) and the compounding assistance device will take a final photograph of the bag (step 11).

Figure 18:
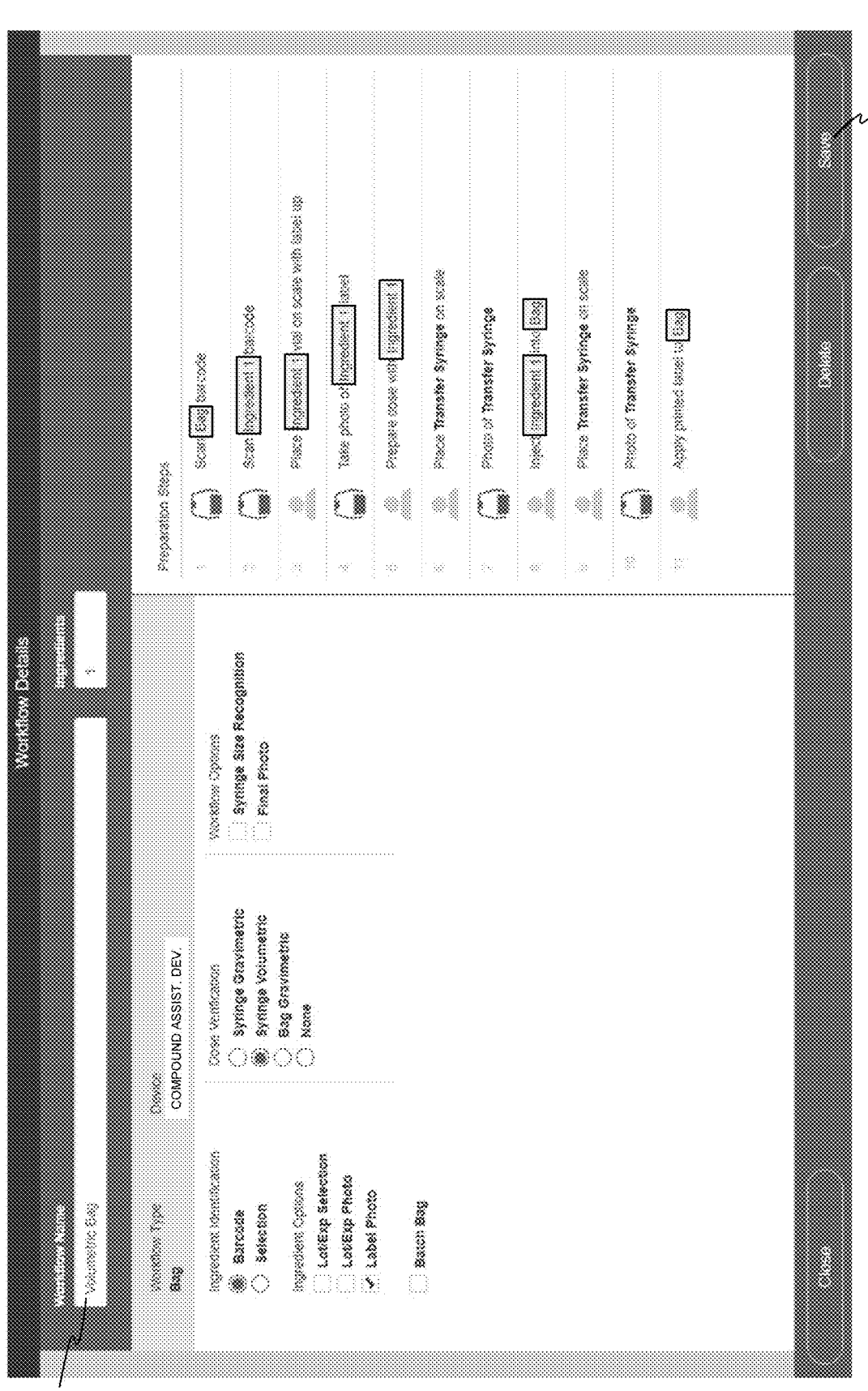
FIG. 18 shows the effect of another option change, in accordance with embodiments of the invention.

FIG. 18 shows the effect of another option change—that of selecting "Syringe Volumetric" instead of "Bag Gravimetric" as the dose verification technique. The requirement of a final photograph has been removed, and a requirement added that a photograph of the vial be taken. As can be seen, the workflow has automatically been adjusted to remove steps specifying that the bag be placed on the scale and weighed (steps 2, 3, 7, and 8 in FIG. 17), and to replace them with steps specifying that the transfer syringe be placed on the scale and photographed (steps 6, 7, 9, and 10 shown in FIG. 18).

In some embodiments, the pharmacist may be given the ability to insert instructional messages into the workflow, to be displayed to an operator during a compounding task. For example, in the workflow of FIG. 18, an instruction to "Call Pharmacist" could be inserted as an additional step in the workflow. Other instructions may relate to a particular delivery vehicle. For example, in a workflow for compounding a pharmaceutical to be delivered in an elastomeric pump, the pharmacist may insert such instructions as "Prime to the tube" or "Attach spike" into the workflow.

The designed workflow can be given a name 1801, and saved 1802 into the workflow database 1405. The new workflow thus becomes available for designing appropriate protocols for compounding specific drugs.

Figure 19:
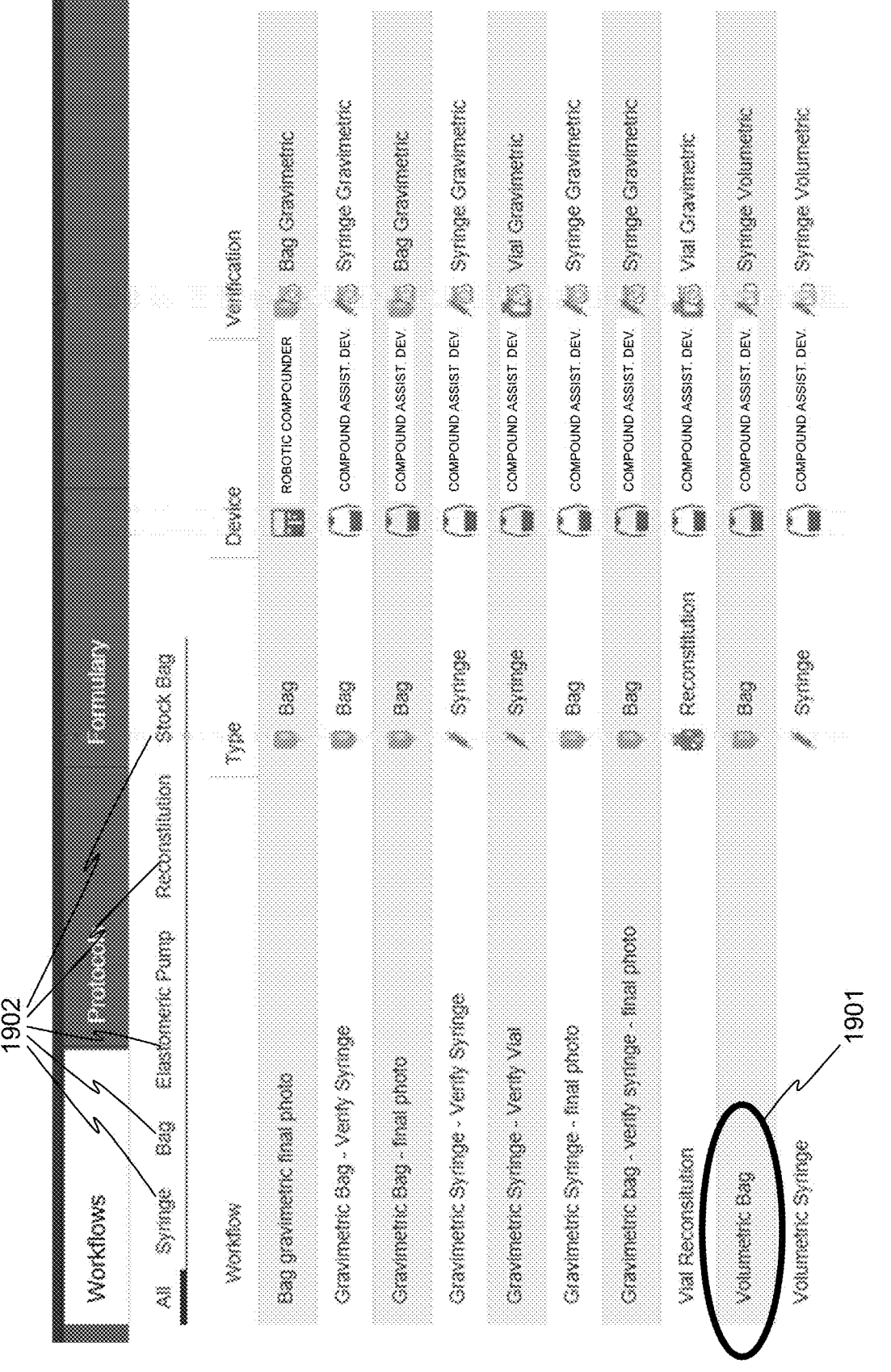
FIG. 19 shows a listing of the defined workflows in a workflow database in accordance with embodiments of the invention.

FIG. 19 shows a listing of the defined workflows in workflow database 1405 in accordance with embodiments of the invention, including the "Volumetric Bag" workflow defined in FIG. 18 and shown at 1901 in FIG. 19. Over time, the number of workflows in workflow database 1405 may grow to be large. Filters 1902 may be provided for displaying only those workflows related to particular delivery options.

Figure 20:
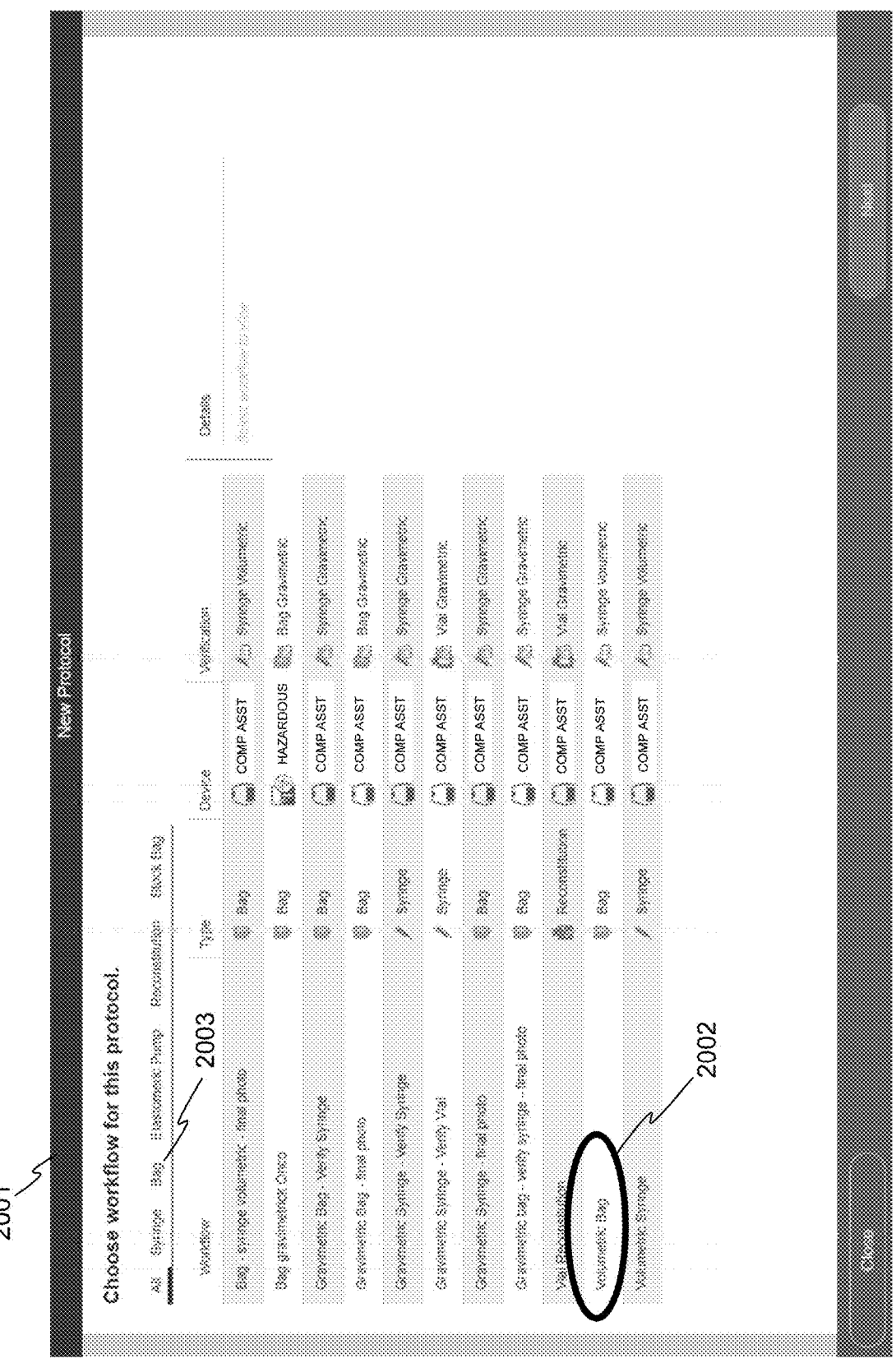
FIG. 20 shows a first user interface screen for creating a protocol, in accordance with embodiments of the invention.

FIG. 20 shows a first user interface screen 2001 for creating a protocol, in accordance with embodiments of the invention. In this example, the first step in creating a protocol is to select a workflow to be referenced, for example the "Volumetric Bag" workflow created above and shown at 2002 in FIG. 20. The protocol designer can choose a workflow appropriate for the drug being compounded and its delivery vehicle. For example, Heparin is conveniently delivered by IV drip from an IV bag.

Figure 21:
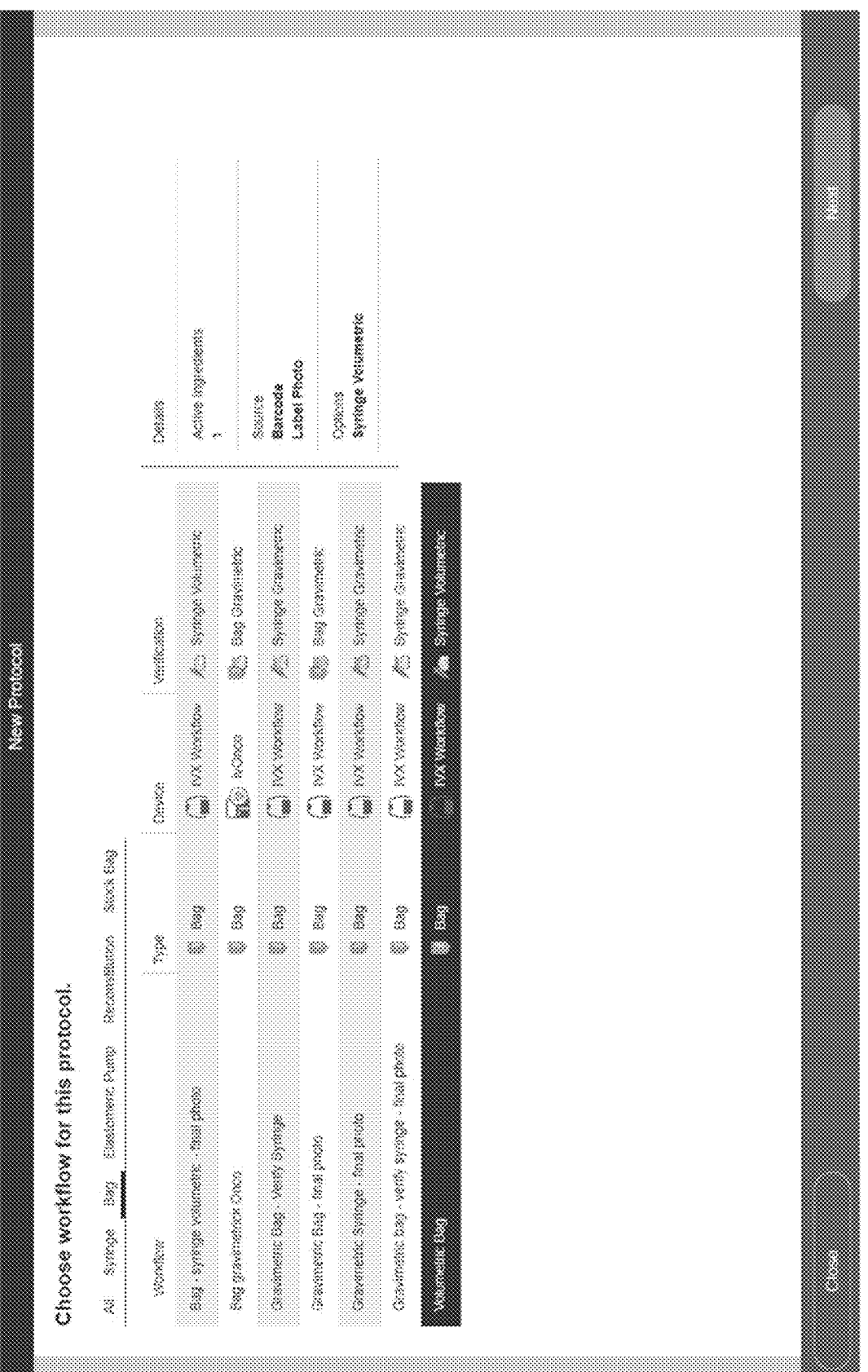
FIG. 21 shows an example result of filtering, in accordance with embodiments of the invention.

Because the system may accumulate a large number of workflows over time, the user may select a filter such as filter 2003, to limit the listed workflows to those applicable to the delivery vehicle that is intended to be used. FIG. 21 shows an example of the result of filtering to display only workflows for bag delivery. In FIG. 21, the "Volumetric Bag" workflow has been selected.

Figure 22:
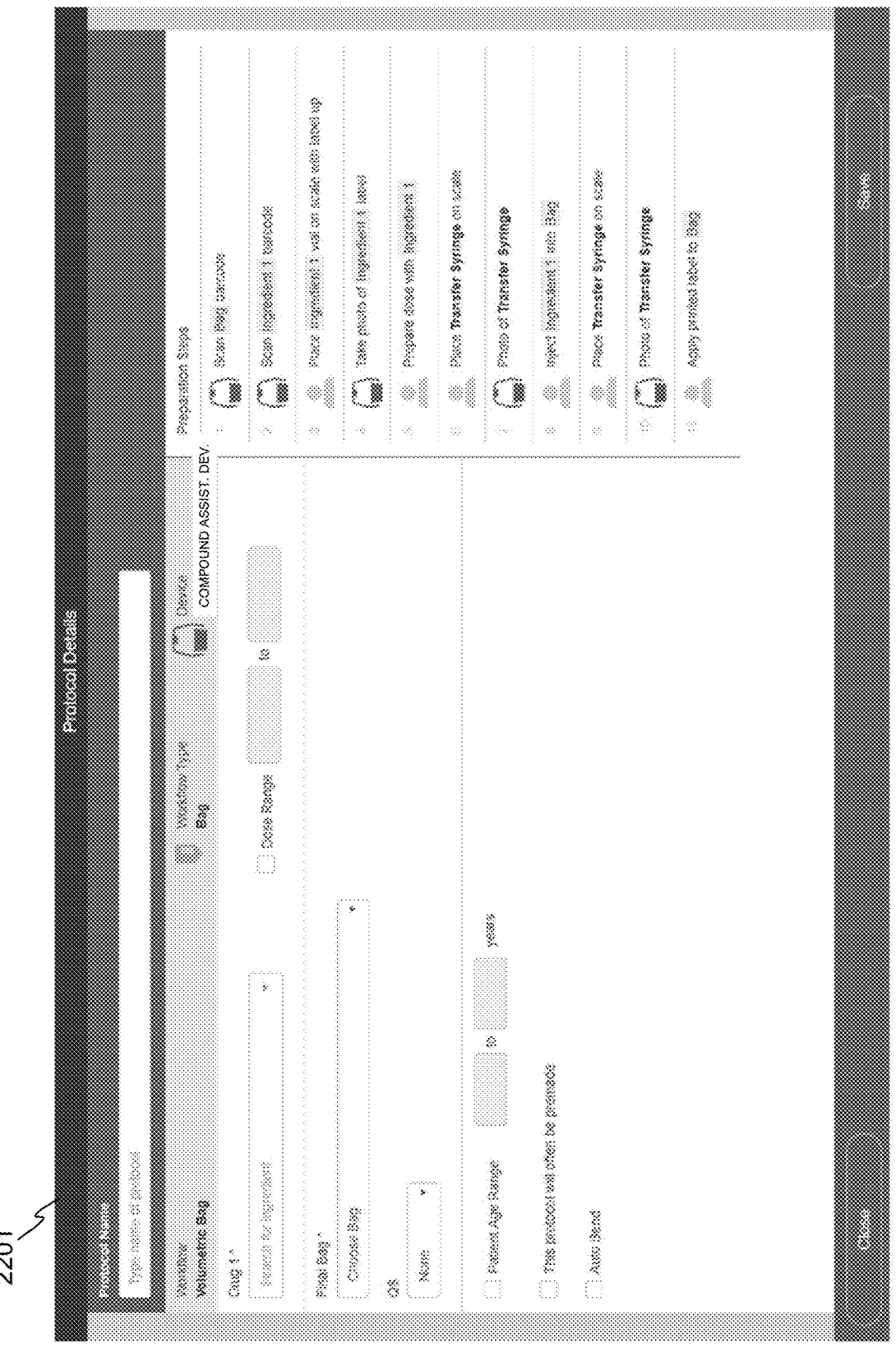
FIG. 22 shows a user interface screen for assigning a pharmaceutical to a workflow, in accordance with embodiments of the invention.

FIG. 22 shows another user interface screen 2201 for assigning a pharmaceutical to the workflow selected on screen 2101, to create a protocol. For an IV drip bag, two "ingredients" are selected—the pharmaceutical to be placed in the bag, and the type of the bag itself. For example bags of different sizes are available, and different bags may contain different diluents.

Figure 23:
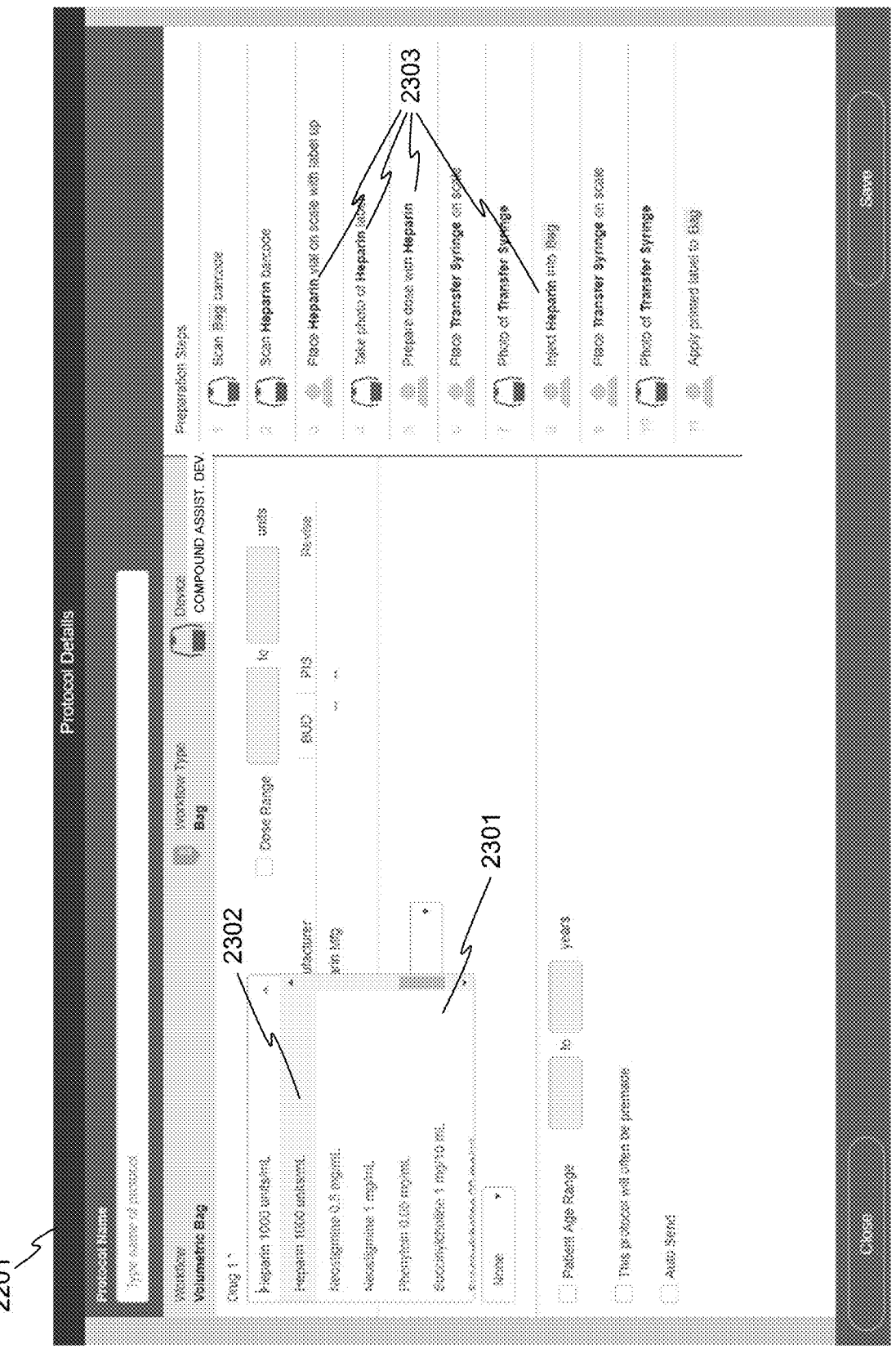
FIG. 23 shows the screen of FIG. 22 in the process of selecting the ingredients for the protocol, in accordance with embodiments of the invention.

FIG. 23 shows screen 2201 in the process of selecting the ingredients for the protocol being designed. A drop-down menu 2301 presents choices for the drug to be compounded. Heparin has been selected at 2302, and is automatically populated into several locations 2303 (not all of which are labeled) in the selected workflow.

Figure 24:
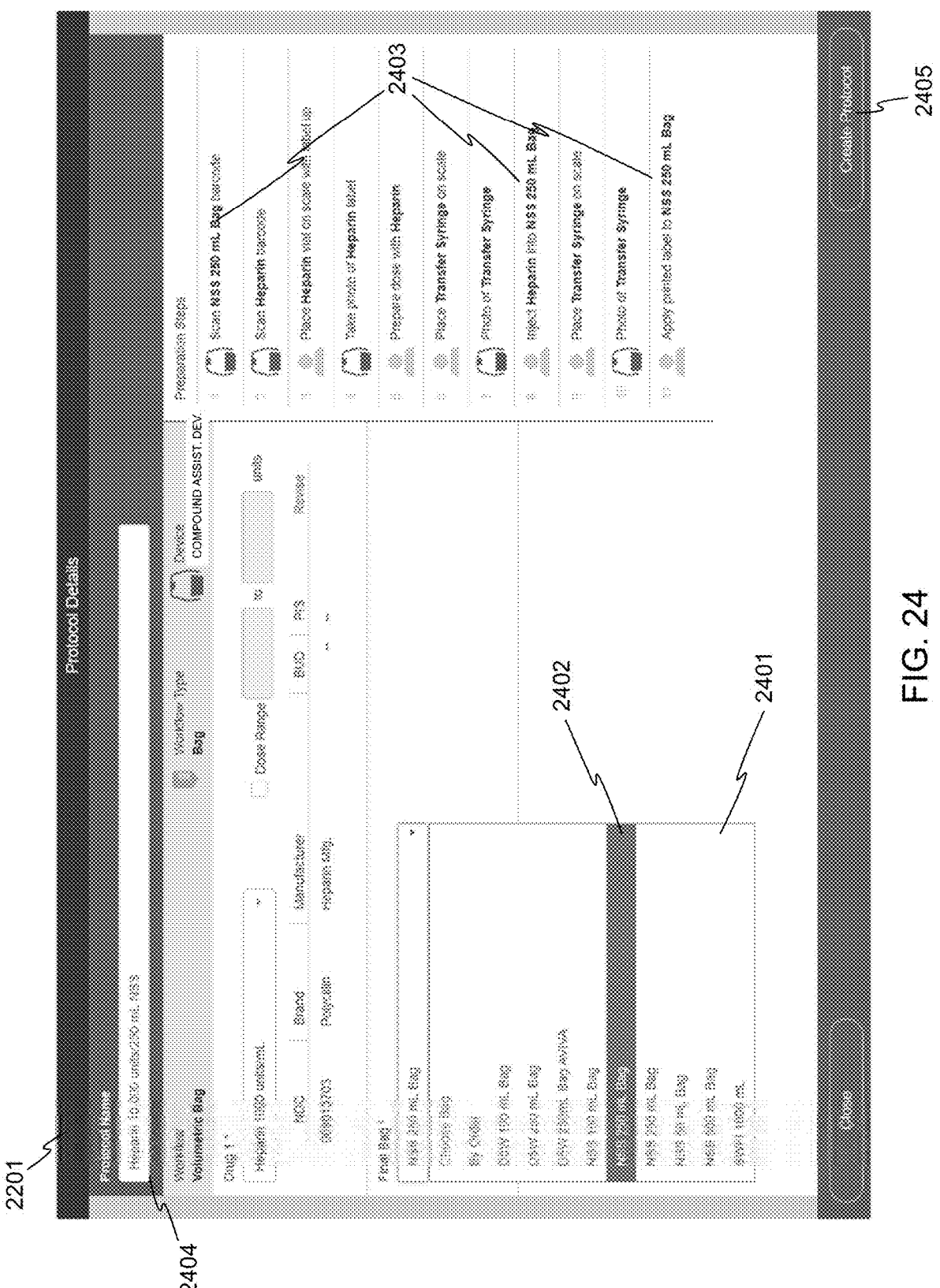
FIG. 24 shows the screen of FIG. 22 in the process of selecting a type of bag to use in the protocol, in accordance with embodiments of the invention.

FIG. 24 shows screen 2201 in the process of selecting the type of bag to use in the protocol. Another drop-down menu 2401 presents choices for the bag type, and a 250 ml bag containing normal saline solution has been selected at 2402. The bag type is automatically populated into the workflow at 2403, completing the protocol. The protocol can be given a name at 2404, and saved at 2405 into protocol database 1406.

Figure 25:
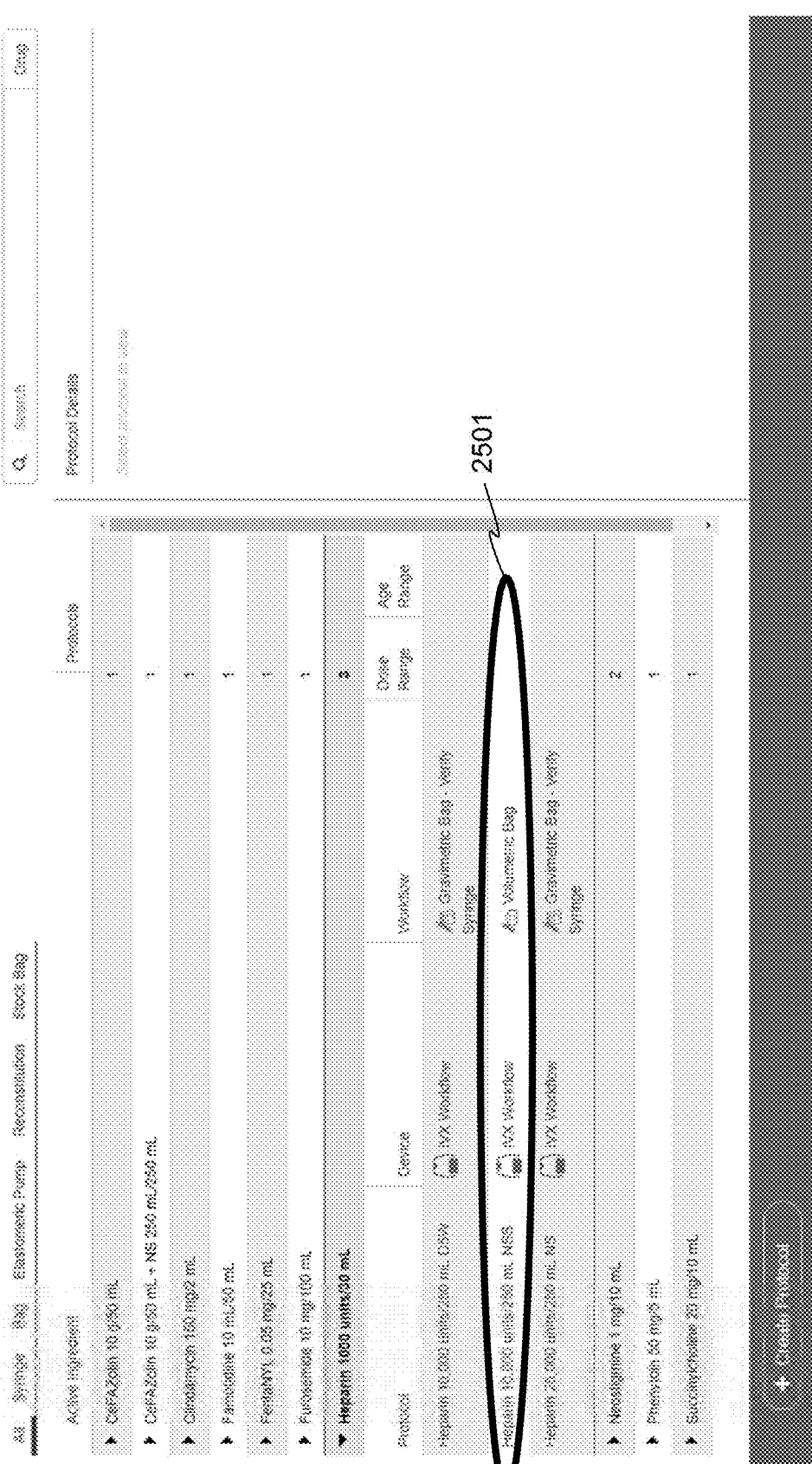
FIG. 25 shows a listing of protocols in a protocol database, in accordance with embodiments of the invention.

FIG. 25 shows a listing of protocols in protocol database 1406, including the newly-created protocol 2501. As is shown in FIG. 25, different protocols may be available for compounding the same drug, for example according to different workflows. If a protocol exists matching a new order, the existing protocol can be selected from the list. If no suitable protocol exists, a new protocol can be created as is described above.

The system preferably presents only choices that are appropriate for the selected workflow. For example, only medications that are compatible with IV drip delivery would be presented on drop-down menu 2301, when a workflow for bag delivery is selected. Thus, time is saved for the protocol designer, and errors may be avoided.

Figure 26:
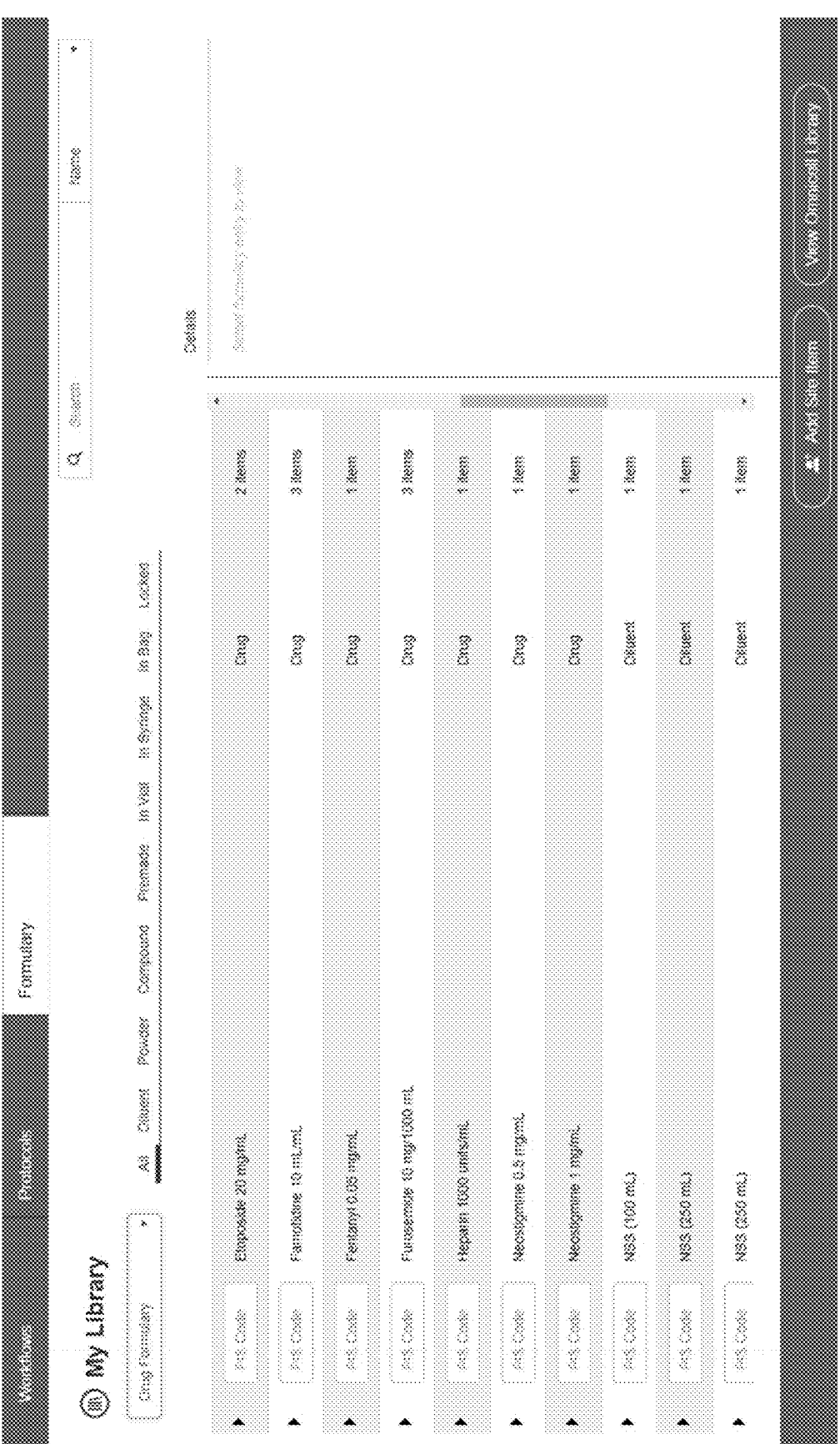
FIG. 26 shows a portion of a formulary database, in accordance with embodiments of the invention.

The system may implement other similar rules as well. For example, the system maintains formulary database 1407, which includes a listing of pharmaceuticals and other items available for use in compounding. FIG. 26 shows a portion of formulary database 1407. Items in the database are also coded by type, for example "Drug" or "Diluent" as shown in FIG. 26. Other types may include "Powder" for powdered drugs. Items may also be coded by the kind of container they are supplied in, for example whether they are supplied to the compounding process in a vial, syringe, or bag. The system may use this information to prevent or eliminate "nonsense" protocols. For example, the system may not present options that would result in the creation of a protocol for delivering a powdered drug in a syringe.

Figure 27:
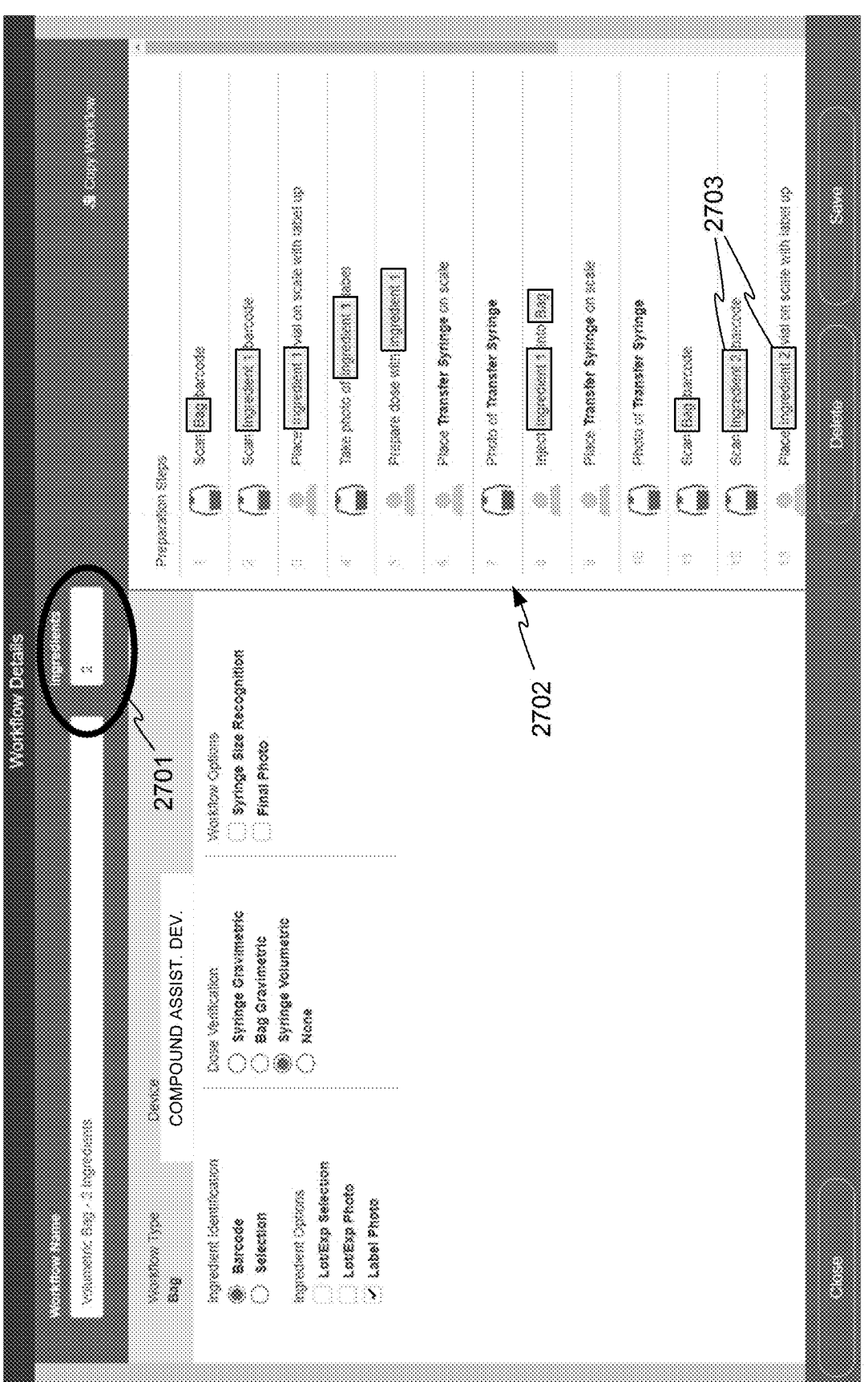
FIG. 27 illustrates the creation of a two-ingredient workflow, in accordance with embodiments of the invention.

While the above examples have involved simple compounding tasks involving only one drug, multi-drug compounding tasks can be specified. For example, multiple drugs may be added to an IV bag, for simultaneous delivery. FIG. 27 illustrates the creation of a two-ingredient workflow similar to the "Volumetric Bag" workflow created earlier (FIG. 18). When two ingredients are specified at 2701, workflow 2702 automatically populates with additional steps for adding the second ingredient to the bag, as shown at 2703. (Additional steps are present but not visible.)

Figure 28:
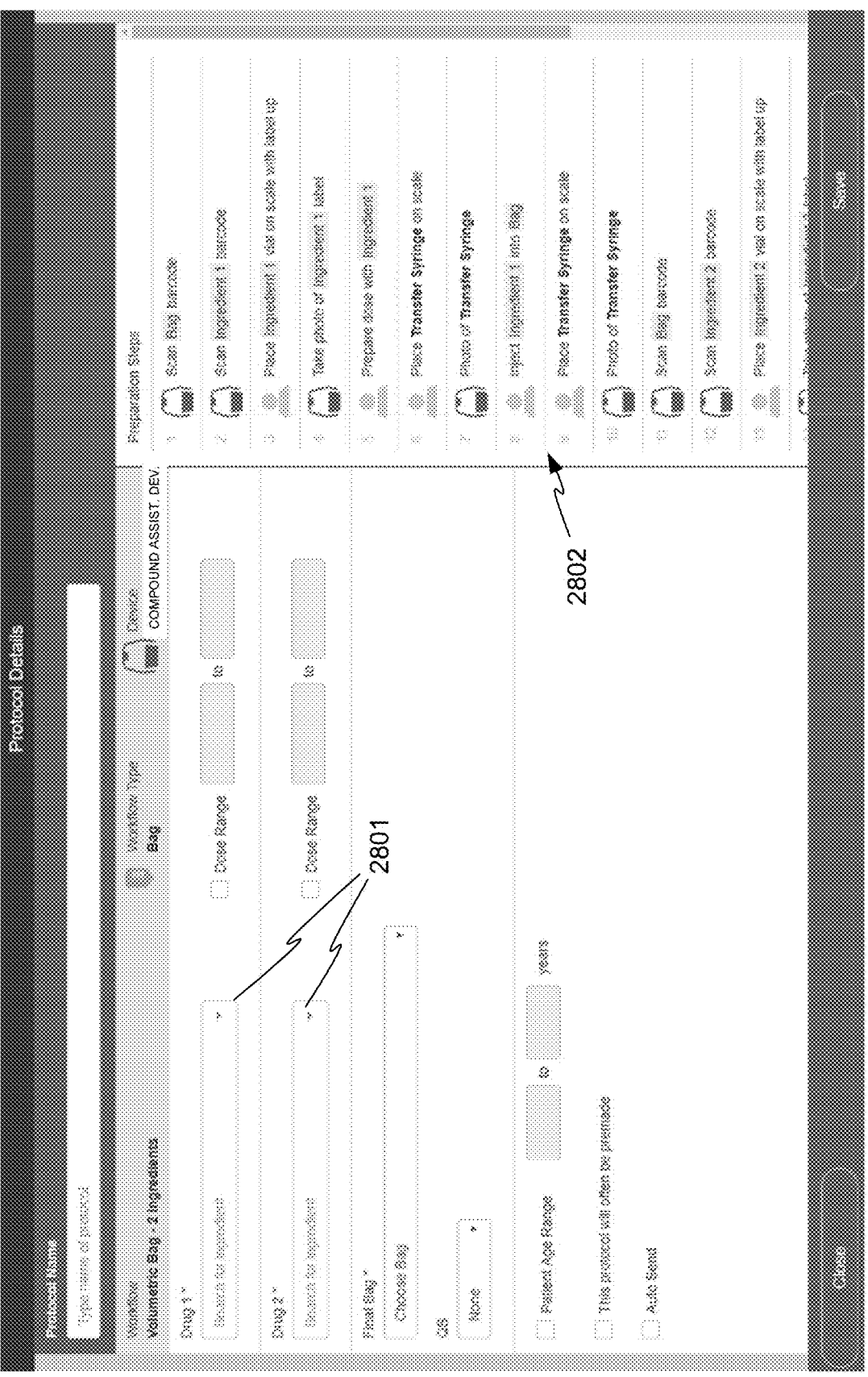
FIG. 28 shows a user interface screen for creating a protocol utilizing the two-ingredient workflow of FIG. 27.

FIG. 28 shows a user interface screen for creating a protocol utilizing the two-ingredient workflow created above. FIG. 28 is similar to FIG. 22, except that two drop-down menus 2801 are provided for specifying the two drugs to be added to the bag. As before, once the ingredients are specified, they are automatically populated into protocol 2802. Any feasible number of ingredients may be incorporated.

Figure 29:
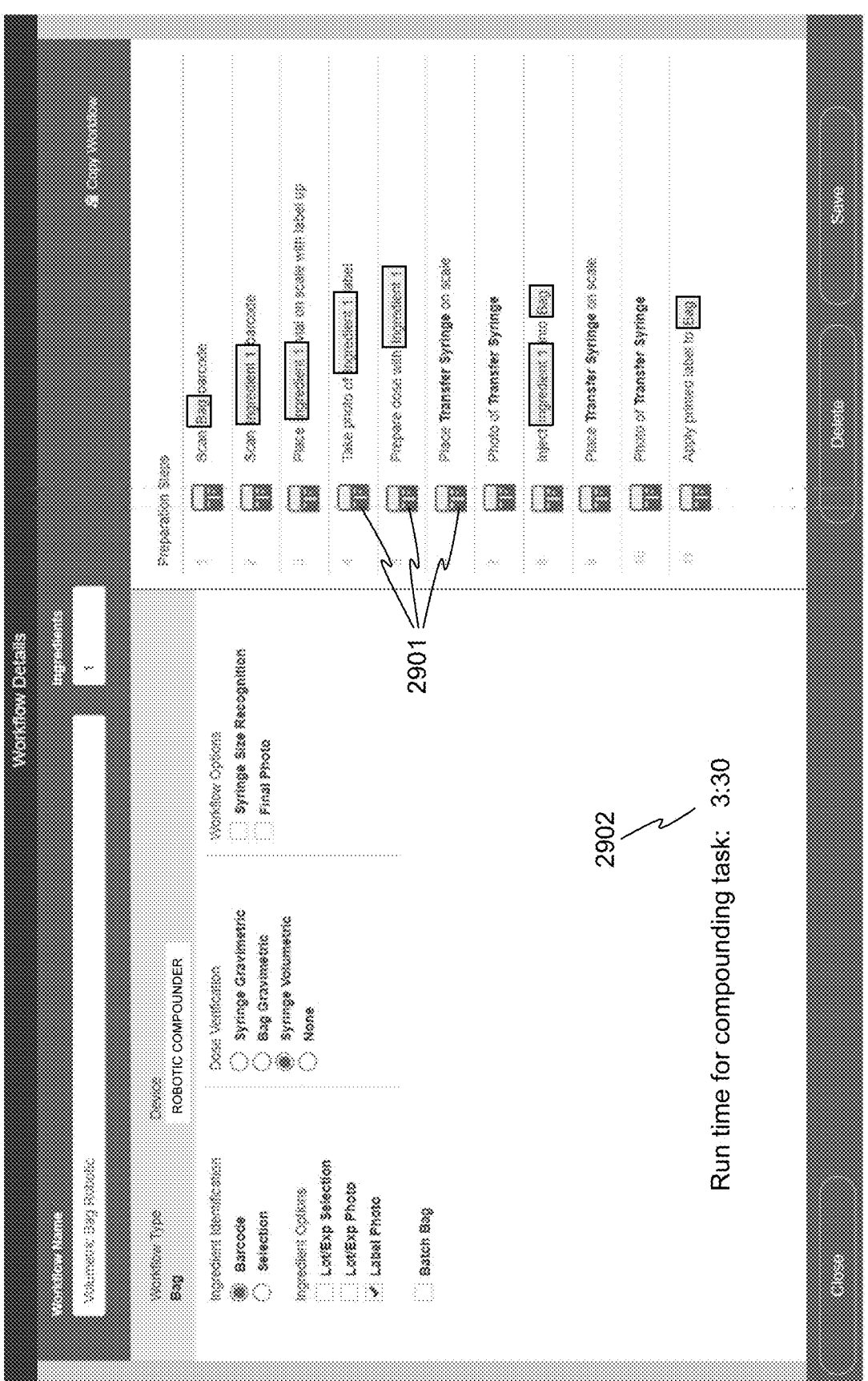
FIG. 29 illustrates the specification of a workflow for robotic compounding, in accordance with embodiments of the invention.

The above examples are also presented in the context of a compounding assistance device such as device 201. Other workflows and protocols may be designed for use in a compounding robot. FIG. 29 illustrates the specification of a workflow for robotic compounding. FIG. 29 is similar to FIG. 18, however all of the steps 2901 are performed robotically, rather than some by a human operator.

Other differences may exist between workflows intended for different compounding devices. For example, verification options may be mutually exclusive in the design of a workflow for one kind of compounding device, but it may be possible to select multiple verification options in designing a workflow for another kind of compounding device. Either manual or automatic compounding may have mutually exclusive verification options or the ability to select multiple verification options.

In addition, the system has estimated the time 2902 required for the robotic compounder to perform the specified sequencing task. The estimated time may be useful to a user in planning his or her own work, or in choosing workflows that accomplish the required compounding and verifications in the least time. The time estimate may be based on the number and kind of steps required to complete the compounding protocol, the number of items used in the compounding task, the distance the items are moved inside the compounding robot, the speed at which the robot moves the items, and other factors. While the time estimate is shown in the figures only in the context of robotic compounding, the time required for compounding using a compounding assistance device such as device 201 can be estimated as well, based on assumptions of the speed of movement of a human operator, measurement of the time required for previous compounding tasks, or other factors.

Figure 30:
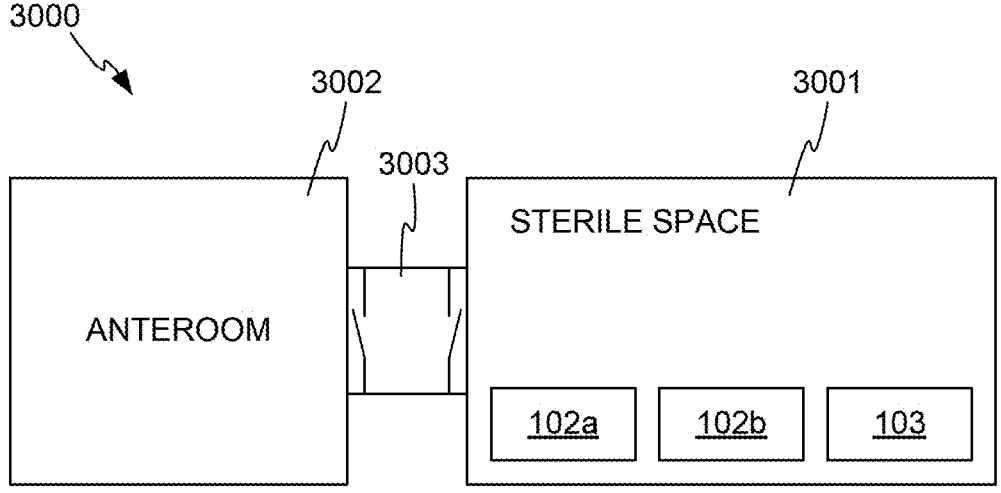
FIG. 30 illustrates a partial organizational diagram of a pharmacy, in accordance with embodiments of the invention.

FIG. 30 illustrates a partial organizational diagram 3000 of a pharmacy in accordance with embodiments of the invention. The pharmacy may be divided into separate spaces, used for different purposes. For example, a sterile space 3001 may house one or more compounding stations such as stations 102a and 102b and one or more robotic compounders 103. Preferably, work involving open pharmaceutical containers is performed in sterile space 3001. Sterile space 3001 is connected to an "anteroom" 3002, which provides a number of functions. For example, unopened pharmaceutical packages and other supplies may be stored or at least temporarily handled in anteroom 3002. Personnel in anteroom 3002 may prepare kits of medications and supplies for specific compounding tasks, to be passed into sterile space 3001 for the actual compounding. Once a compounding task is completed, the resulting sealed container holding the compounded formulation can be passed back to anteroom 3002. Sterile space 3001 and anteroom 3002 may be separated by an airlock 3003 through which materials are passed.

In some situations, personnel in anteroom 3002 may be able to fulfill medication orders without involving personnel in sterile space 3001. For example, some medications may be "premade" and stored in or brought into anteroom 3002. Premade medications may be compounded formulations that are used commonly enough to justify accumulating a supply of them in anticipation of use, rather than compounding them for each individual order. When an order for such a medication is received, the order may simply be fulfilled in the anteroom from existing stock.

Formulations may be premade by a manufacturer and received by the pharmacy in their completed form, or may be locally premade in advance of anticipated use. For example, commonly-used formulations may be prepared in batches in sterile space 3001 during off hours or when compounding capacity is otherwise available in the pharmacy. The batch size may be selected based on a number of factors, including historical trends in the use of a particular medication, and the shelf life of the compounded formulation (also called the "beyond use" date or time).

Embodiments of the invention provide for the handling of premade medications in a manner that is conceptually similar to the handling of individually-compounded medications.

For example, drugs, diluents, and the like may often be added to the formulary list, so that they become available for compounding. In some cases, a drug may be purchased from a manufacturer in completed form, so that no compounding is necessary. When the drug is added to the formulary, it can be flagged as manufacturer premade. For example, a simple check box, radio button, or other user interface selection may be provided in the system user interface for this indication. As part of adding the drug to the formulary, a "virtual protocol" can be created and stored in the protocol listing for later use. The virtual protocol would not include compounding steps, but would flag an order for filling from stock in the anteroom.

Figure 31:
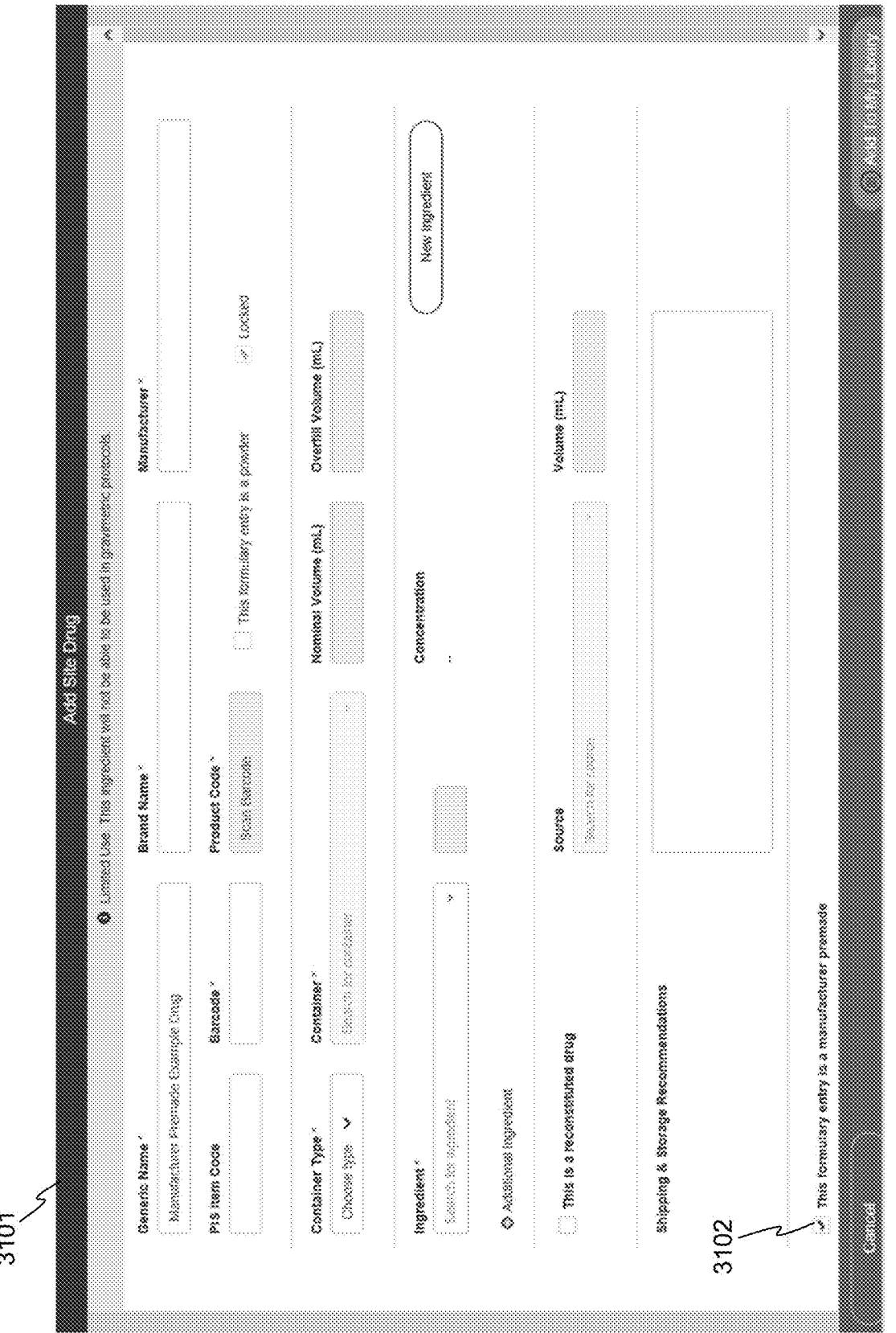
FIG. 31 shows a user interface screen, for adding a drug to the formulary, in accordance with embodiments of the invention.

FIG. 31 shows a user interface screen 3101 for adding a drug to the formulary, in accordance with embodiments of the invention. Screen 3101 includes various fields for providing information about the drug being added to the formulary, but screen 3101 has not been completed in this example, other than checking the box 3102 to indicate that the drug is a manufacturer premade drug.

Figure 32:
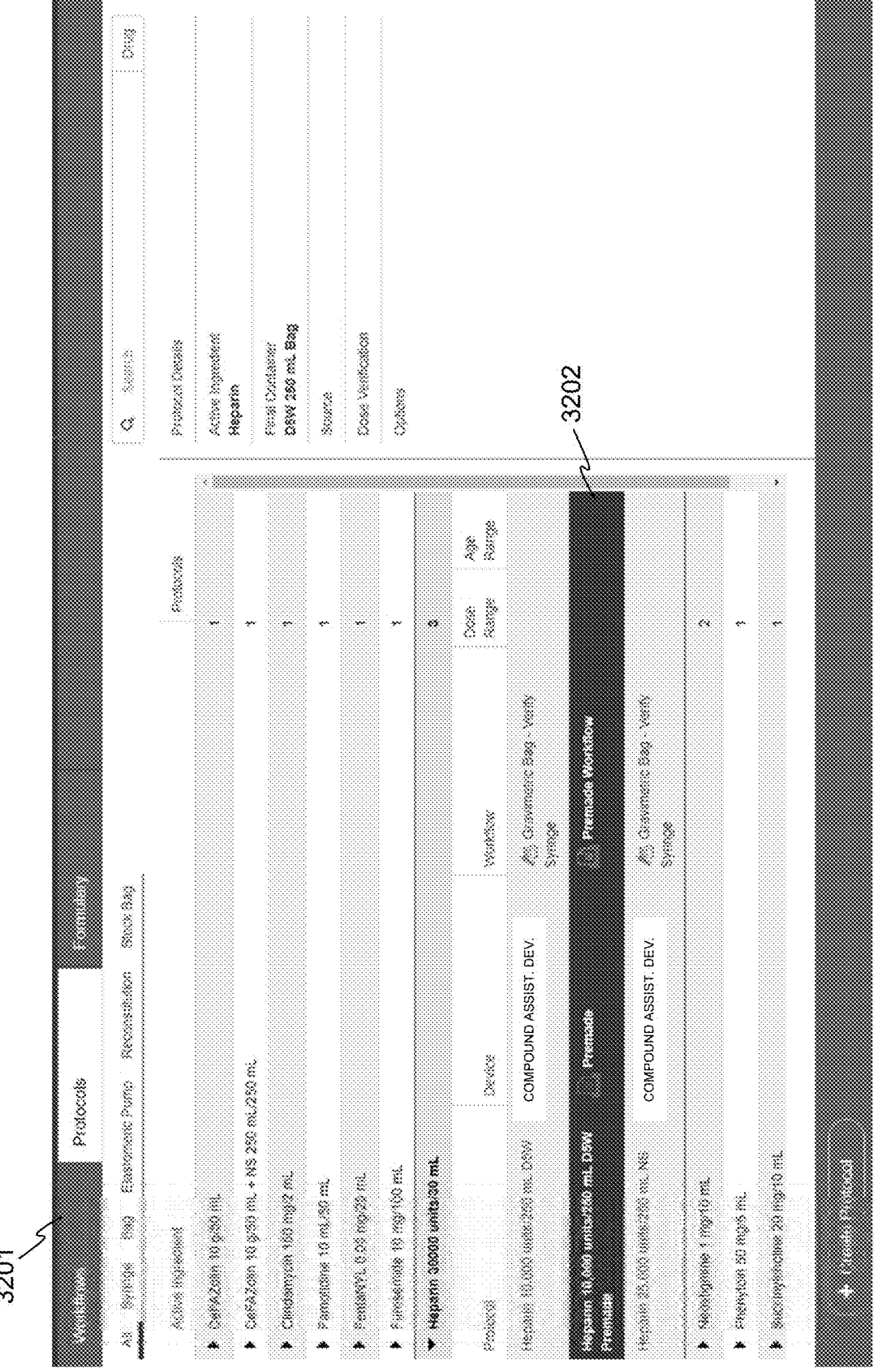
FIG. 32 shows a user interface screen with a listing of protocols, including a virtual protocol in accordance with embodiments of the invention.

FIG. 32 shows a user interface screen 3201 with a partial listing of protocols in the system. A virtual protocol 3202 is highlighted, and indicates that it relates to a premade drug.

Figure 33:
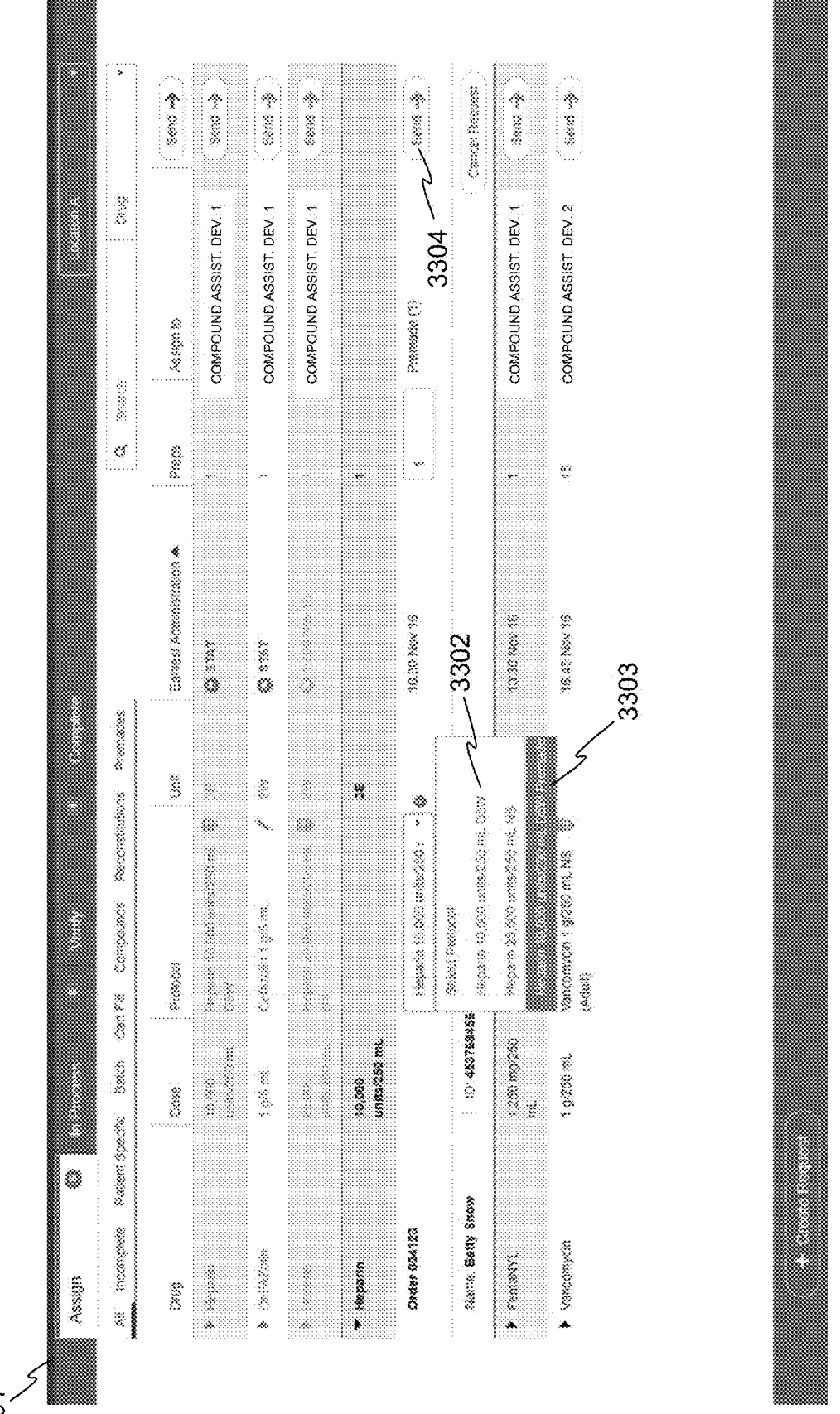
FIG. 33 shows a user interface screen for assigning the preparation of a compounded drug, in accordance with embodiments of the invention.

Later, when the drug has been prescribed and ordered from the pharmacy, the virtual "protocol" of simply filling the order from stock is presented as an option in the compounding workflow process, possibly alongside one or more actual protocols for compounding the same drug locally. For example, FIG. 33 shows a user interface screen 3301 for assigning the preparation of a compounded drug, in accordance with embodiments of the invention—in this example 10,000 units of Heparin. A protocol 3302 for preparing this dose (in a 250 ml bag having D5W as a diluent) exists, and is presented to the pharmacist as an option for on-site compounding.

However, the system has also recognized that the pharmacy stocks a manufacturer-premade version of this drug, and presents a "protocol" 3303 for it as well. In this case, the "protocol" is virtual, and serves only as a flag to the personnel in the anteroom to intercept this assignment and fill the order using the manufacturer premade version. In FIG. 33, the pharmacist has selected virtual protocol 3303, and can forward the assignment using the "Send" button 3304, or a similar user interface control.

Had the pharmacist selected the normal protocol for on-site compounding, the assignment would not be intercepted, and the compounding task would have been assigned to one of the compounding devices for processing. From the point of view of the pharmacist, specifying a premade drug is conceptually very similar to specifying that a drug be compounded on-site.

A similar virtual protocol may be created when a batch formulation is prepared. The virtual protocol can be presented to the pharmacist as an option for assigning a compounding task, similar to the presentation in FIG. 33.

In other embodiments, when the pharmacist specifies a compounding protocol for which a batch was recently prepared, the system may automatically recognize that a supply of batch-prepared drug is on hand, and may by default automatically intercept the assignment for filling from stock in the anteroom rather than sending the protocol to a compounding device for preparation. Preferably, the pharmacist can override this default if desired, and direct fresh compounding.

While the examples above have been given in the context of compounding of medications for intravenous (IV) delivery, the principles involved are applicable in other contexts as well. For example, in neonatal and pediatric care, medicines are often given to infants and children orally in liquid form. This may be true even for medications that might often be given to older patients in pill or other form, for example acetaminophen. Preparation of oral liquid medication doses may be considered a type of medication compounding, performed in accordance with a workflow. For example, a powdered medication may be dissolved into a liquid for oral delivery, or a concentrated liquid medication may be diluted to a particular dosage appropriate for the age or size of the patient.

Workflows and protocols can be created using the techniques described above for the preparation of medications for delivery as oral liquids. As with medications formulated and packaged for IV delivery, a medication may be prepared in liquid form for a specific patient, may be premade locally, or may be purchased premade from a supplier. In the case of premades, virtual protocols may be constructed as described above.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. It is to be understood that any workable combination of the elements and features disclosed herein is also considered to be disclosed.

The invention has now been described in detail for the purposes of clarity and understanding. However, those skilled in the art will appreciate that certain changes and modifications may be practiced within the scope of the appended claims.

What is claimed is:

1. A method of compounding a medication, the method comprising:

presenting, at a user interface presented on an electronic display, a list of a number of workflow types differentiated at least in part by a kind of delivery vehicle in which a completed compounded pharmaceutical is to be delivered;

receiving, via a user input device, a first user selection of one of the number of workflow types;

presenting, at the user interface, a list of a number of compounding device types that are available for use with the selected workflow type;

receiving, via the user input device, a second user selection of one of the number of compounding device types;

presenting, at the user interface, a number of options applicable to compounding a pharmaceutical on the selected compounding device type into the delivery vehicle of the selected workflow type;

receiving, via the user input device, a third user selection of one or more of the options;

presenting, in the user interface, an automatically constructed workflow for compounding a pharmaceutical into the delivery vehicle of the selected workflow type on the selected compounding device type;

receiving, via the user input device, a fourth user selection that specifies a particular pharmaceutical to be compounded according to the constructed workflow;

receiving an automatically constructed compounding protocol constructed from the constructed workflow;

causing the compounding protocol to be transmitted to a robotic compounding device of the selected compounding device type; and causing the robotic compounding device to compound the specified pharmaceutical into the delivery vehicle of the selected workflow type in accordance with the compounding protocol, wherein during compounding the specified pharmaceutical, the robotic compounding device verifies that the delivery vehicle matches the selected workflow type, transfers a correct volume of the specified pharmaceutical, into the delivery vehicle, and verifies that the correct volume of the specified pharmaceutical has been transferred to the delivery vehicle.

2. The method of claim 1, wherein:
causing the specified pharmaceutical to be compounded into the delivery vehicle of the selected workflow type comprises compounding the specified pharmaceutical into a container suitable for intravenous delivery of the specified pharmaceutical.

3. The method of claim 1, wherein:
causing the specified pharmaceutical to be compounded into the delivery vehicle of the selected workflow type comprises compounding the specified pharmaceutical into a container suitable for oral liquid delivery of the specified pharmaceutical.

4. The method of claim 1, wherein:
the workflow comprises placeholders for information to be determined by a specific pharmaceutical to be compounded according to the constructed workflow.

5. The method of claim 1, further comprising:
saving the compounding protocol to a workflow database.

6. The method of claim 1, wherein:
causing the specified pharmaceutical to be compounded into the delivery vehicle of the selected workflow type comprises causing a compounding robot to perform at least one step of the compounding protocol.

7. The method of claim 1, wherein:
causing the specified pharmaceutical to be compounded into the delivery vehicle of the selected workflow type comprises causing a compounding robot to perform each step of the compounding protocol.

8. The method of claim 1, wherein:
causing the specified pharmaceutical to be compounded into the delivery vehicle of the selected workflow type comprises:
receiving user credentials from a reviewing party; and
receiving a verification confirmation associated with the compounding protocol from the reviewing party.

9. The method of claim 8, wherein:
causing the specified pharmaceutical to be compounded into the delivery vehicle of the selected workflow type further comprises causing verification information to be presented on a remote device upon receiving the user credentials.

10. The method of claim 1, further comprising:
automatically generating the constructed workflow based on the first user selection, the second user selection, the third user selection, and the fourth user selection.

11. A system for pharmaceutical compounding, comprising:
one or more processors;
an electronic display; and
memory holding instructions that, when executed by the one or more processors, cause the system to:
present, at a user interface presented on the electronic display, a list of a number of workflow types differentiated at least in part by a kind of delivery vehicle in which a completed compounded pharmaceutical is to be delivered;
receive, via a user input device, a first user selection of one of the number of workflow types;
present, at the user interface, a list of a number of compounding device types;

receive, via the user input device, a second user selection of one of the number of compounding device types;
present, at the user interface, a number of options applicable to compounding a pharmaceutical on the selected compounding device type into the delivery vehicle of the selected workflow type;
receive, via the user input device, a third user selection of one or more of the options;
present, in the user interface, an automatically constructed workflow for compounding a pharmaceutical into the delivery vehicle of the selected workflow type on the selected compounding device type;
receive, via the user input device, a fourth user selection that specifies a particular pharmaceutical to be compounded according to the constructed workflow;
receive an automatically constructed compounding protocol constructed from the constructed workflow;
cause the compounding protocol to be transmitted to a robotic compounding device of the selected compounding device type; and
cause the robotic compounding device to compound the specified pharmaceutical into the delivery vehicle of the selected workflow type in accordance with the compounding protocol, wherein during compounding the specified pharmaceutical, the robotic compounding device verifies that the delivery vehicle matches the selected workflow type, transfers a correct volume of the specified pharmaceutical into the delivery vehicle, and verifies that the correct volume of the specified pharmaceutical has been transferred to the delivery vehicle.

12. The system for pharmaceutical compounding of claim 11, wherein the instructions cause the system to:
receive an input at the user interface that comprises instructional messages to be displayed to an operator during a compounding task.

13. The system for pharmaceutical compounding of claim 11, wherein the instructions cause the system to:
receive a fifth user selection of a specific delivery vehicle; and
filter the number of options to remove workflows that are not associated with the specific delivery vehicle.

14. The system for pharmaceutical compounding of claim 11, wherein the instructions cause the system to:
prevent incompatible compounding protocols from being created.

15. The system for pharmaceutical compounding of claim 11, wherein:
the one or more options comprise a plurality of available dose verification techniques.

16. The system for pharmaceutical compounding of claim 11, wherein:
the compounding protocol is constructed from the constructed workflow by inserting information about the particular pharmaceutical into the constructed workflow.

17. The system for pharmaceutical compounding of claim 11, wherein the instructions cause the system to:
calculate an estimated time for at least one compounding task; and
present the estimated time on the user interface.

18. The system for pharmaceutical compounding of claim 11, wherein:
the one or more options comprise a plurality of available ingredient identification techniques.

19. The system for pharmaceutical compounding of claim 11, wherein:

the compounding device types comprise one or both of a compounding assistance device and a robotic compounder.

20. The system for pharmaceutical compounding of claim 19, wherein:

the robotic compounder is specifically configured for handling dangerous drugs.

\* \* \* \* \*